United States Patent [19]

Felix et al.

[11] Patent Number: 4,504,415

[45] Date of Patent: Mar. 12, 1985

[54] SYNTHESIS OF THYMOSIN ALPHA$_1$ AND DESACETYL THYMOSIN ALPHA$_1$

[75] Inventors: Arthur M. Felix, West Caldwell, N.J.; Dieter Gillessen, Pratteln; Rolf Studer, Bottmingen, both of Switzerland; Johannes A. Meienhofer, Upper Montclair, N.J.; Arnold Trzeciak, Schopfheim, Fed. Rep. of Germany Hoffmann-La Roche Inc., Nutley, N.J.

[21] Appl. No.: 482,114

[22] Filed: Apr. 4, 1983

[51] Int. Cl.$^3$ ............................................ C07C 103/52
[52] U.S. Cl. ............................................ 260/112.5 R
[58] Field of Search .................. 260/112.5 R; 424/177

[56] References Cited

U.S. PATENT DOCUMENTS

| | | | |
|---|---|---|---|
| 4,079,127 | 3/1978 | Goldstein et al. | 424/177 |
| 4,116,951 | 9/1978 | Wang | 260/112.5 R |
| 4,148,788 | 4/1979 | Wang | 260/112.5 R |
| 4,353,821 | 10/1982 | Birr et al. | 260/112.5 R |

OTHER PUBLICATIONS

Birr et al., *Angew. Chem. Int. Ed. Engl.*, 18(5), 394–395, (1979).
Abiko et al., *Chem. Pharm. Bull.*, 30(5), 1776–1783, (1982).
Wang et al., *J. Am. Chem. Soc.*, 101(1), 253–254, (1979).

*Primary Examiner*—Delbert R. Phillips
*Assistant Examiner*—F. T. Moezic
*Attorney, Agent, or Firm*—Jon S. Saxe; Bernard S. Leon; George M. Gould

[57] ABSTRACT

An improved solution phase synthesis of thymosin $\alpha_1$ and desacetyl thymosin $\alpha_1$ with t-Boc side chain protection and proceeding through novel intermediates is disclosed.

5 Claims, 8 Drawing Figures

FIG. 2 SYNTHESIS OF FRAGMENT I

SYNTHESIS OF FRAGMENT II

SYNTHESIS OF FRAGMENT IV

SYNTHESIS OF FRAGMENT III

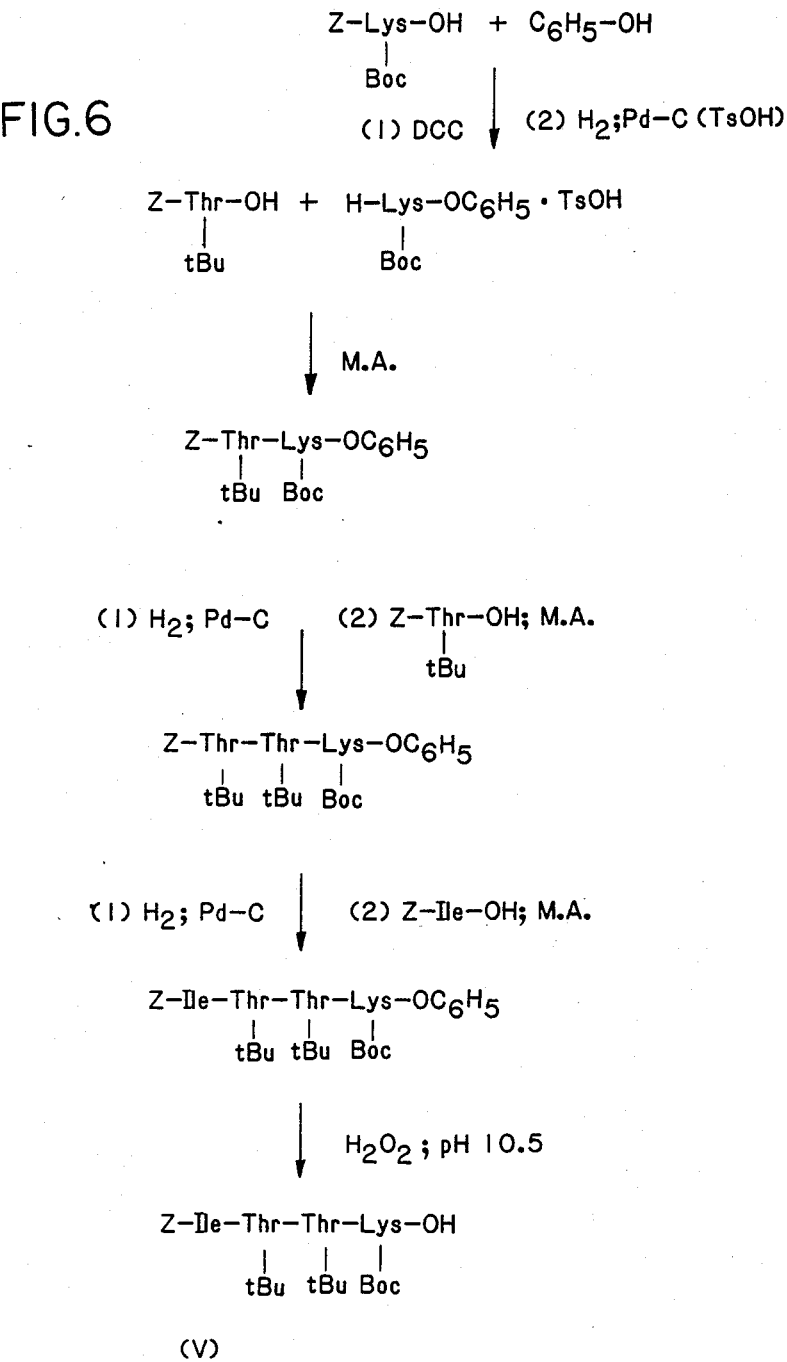
FIG.6 SYNTHESIS OF FRAGMENT V

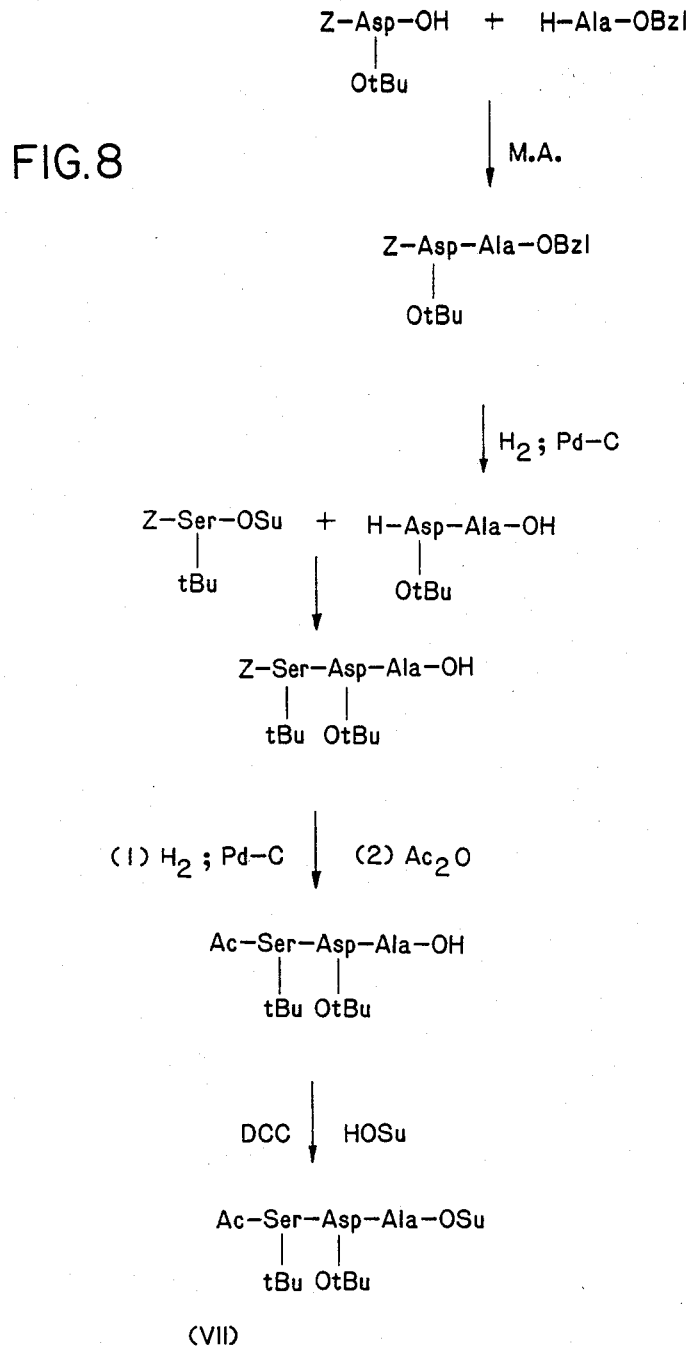
FIG. 8 SYNTHESIS OF FRAGMENT VII

SYNTHESIS OF THYMOSIN $\alpha_1$ AND DESACETYL THYMOSIN $\alpha_1$

BACKGROUND OF THE INVENTION

The isolation of biologically important peptides from the thymus gland has been studied extensively in the last few years. Several peptides have been shown to play certain roles in T-cell maturation. Thymosin $\alpha_1$, a highly acidic acetyl octacosapeptide isolated from calf thymus gland and characterized by sequence analysis has been reported to exhibit biological activities involved in the development of thymus-dependent lymphocytes (T-cells). Desacetyl thymosin $\alpha_1$ has been reported to exhibit the same biological activity as thymosin $\alpha_1$ and further can act as an intermediate in the preparation of thymosin $\alpha_1$.

The isolation and characterization of thymosin $\alpha_1$ was disclosed in U.S. Pat. No. 4,079,127. Synthesis of this peptide by solution and solid phase procedures was disclosed in U.S. Pat. No. 4,148,788.

An alternate solution phase synthesis for thymosin $\alpha_1$ employing a different synthetic strategy was described by Birr and Stollenwerk, Angew. Chem.Int.Ed.Engl. 18, 394 (1979).

A solid phase synthesis of desacetyl thymosin $\alpha_1$ was described by Merrifield et al. at the Fifteenth European Peptide Symposium (Poland) in September, 1978 and was published in the Proceedings of the Fifteenth European Peptide Symposium published June 1979. It was also described by Merrifield in the Alan E. Pierce Award Lecture on Solid Phase synthesis at the 6th American Peptide Symposium given June 20, 1979 and published December, 1979. See also these authors Biochem. 19, 3233 (1980).

In addition, the biosynthesis of desacetyl thymosin $\alpha_1$ by a recombinant microorganism constructed by use of recombinant DNA technology has been described by Crea and Wetzel, U.S. patent application Ser. No. 125,685, filed Feb. 28, 1980.

BRIEF DESCRIPTION OF THE INVENTION

The present invention relates to an improved process for the preparation of thymosin $\alpha_1$ and desacetylthymosin $\alpha_1$. This process involves the use of solution phase peptide synthetic techniques to accomplish the synthesis of seven protected fragment precursors which in turn are used to prepare two key intermediates, the amino terminus decapeptide and the carboxy terminus octadecapeptide.

A further aspect of the invention involves the use of tert-butyl as side chain protecting groups. This allows use of mild acid hydrolysis of the protective groups from the protected precursor compound to the desired end products and thereby avoids the use of final deprotection with very strong acid such as liquid HF which can cause extensive degradation of the product. The instant process thus provides a highly efficient procedure for producing the desired thymosin $\alpha_1$ and desacetylthymosin $\alpha_1$ in higher yield than heretofore been possible.

DESCRIPTION OF THE DRAWINGS

FIG. 6 sets forth the procedure used to synthesize fragment V.

FIG. 8 sets forth the procedure used to synthesize fragment VII.

In FIG. 1 the fragments designated by roman numerals represent the seven starting fragments used in the synthesis while arabic numerals indicate intermediates produced and used in the synthesis. It should be noted that while the synthesis has been described in relation to the preparation of thymosin $\alpha_1$, the same overall strategy is employed to produce desacetyl thymosin $\alpha_1$ with the minor modification that Boc-Ser(t-Bu)-Asp(OtBu)-Ala-OSu is substituted for fragment VII.

DESCRIPTION OF THE INVENTION

Figure 1:
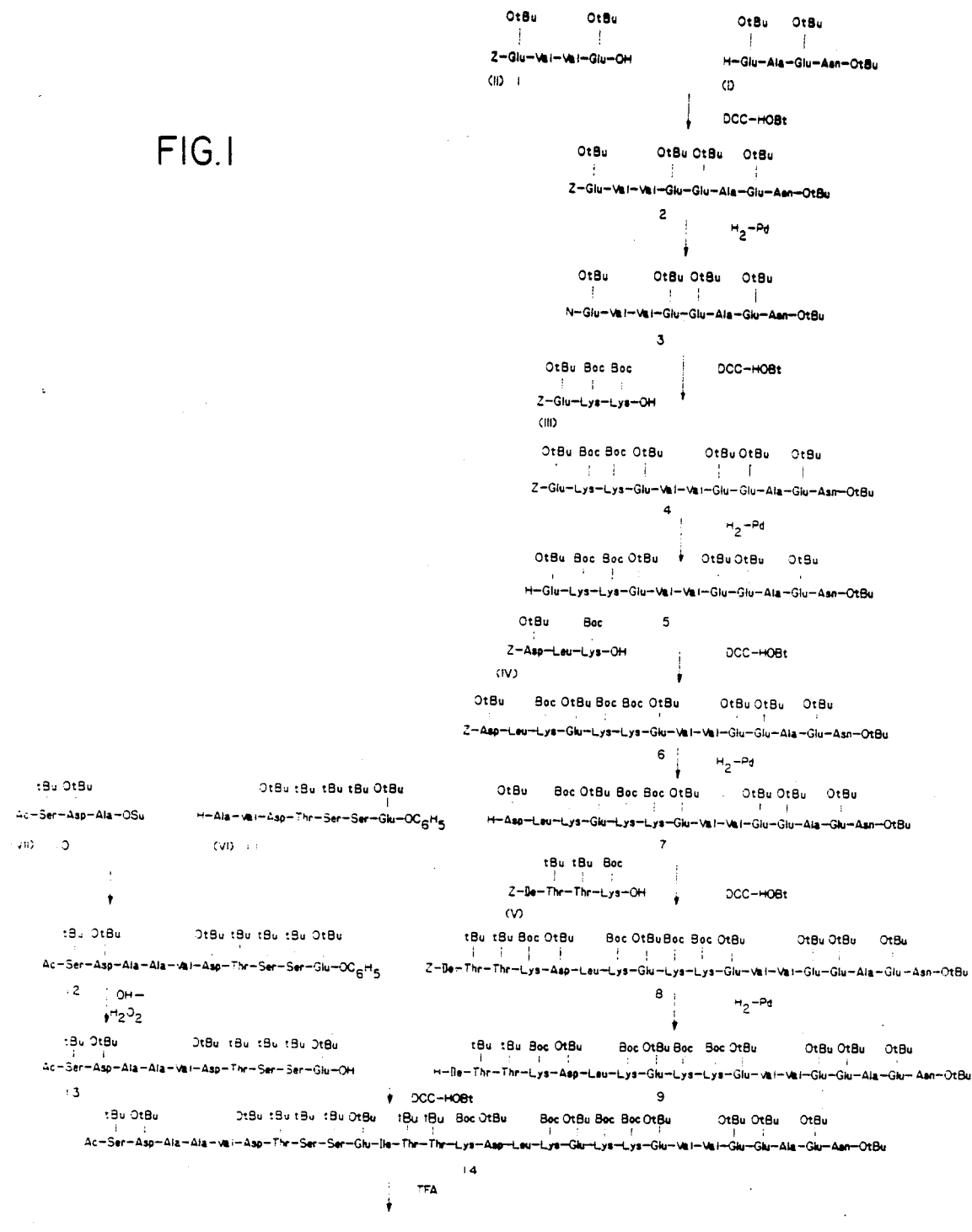
FIG. 1 sets forth the synthesis strategy for thymosin $\alpha_1$ from seven protected peptide fragments (I-VII).
Figure 2:
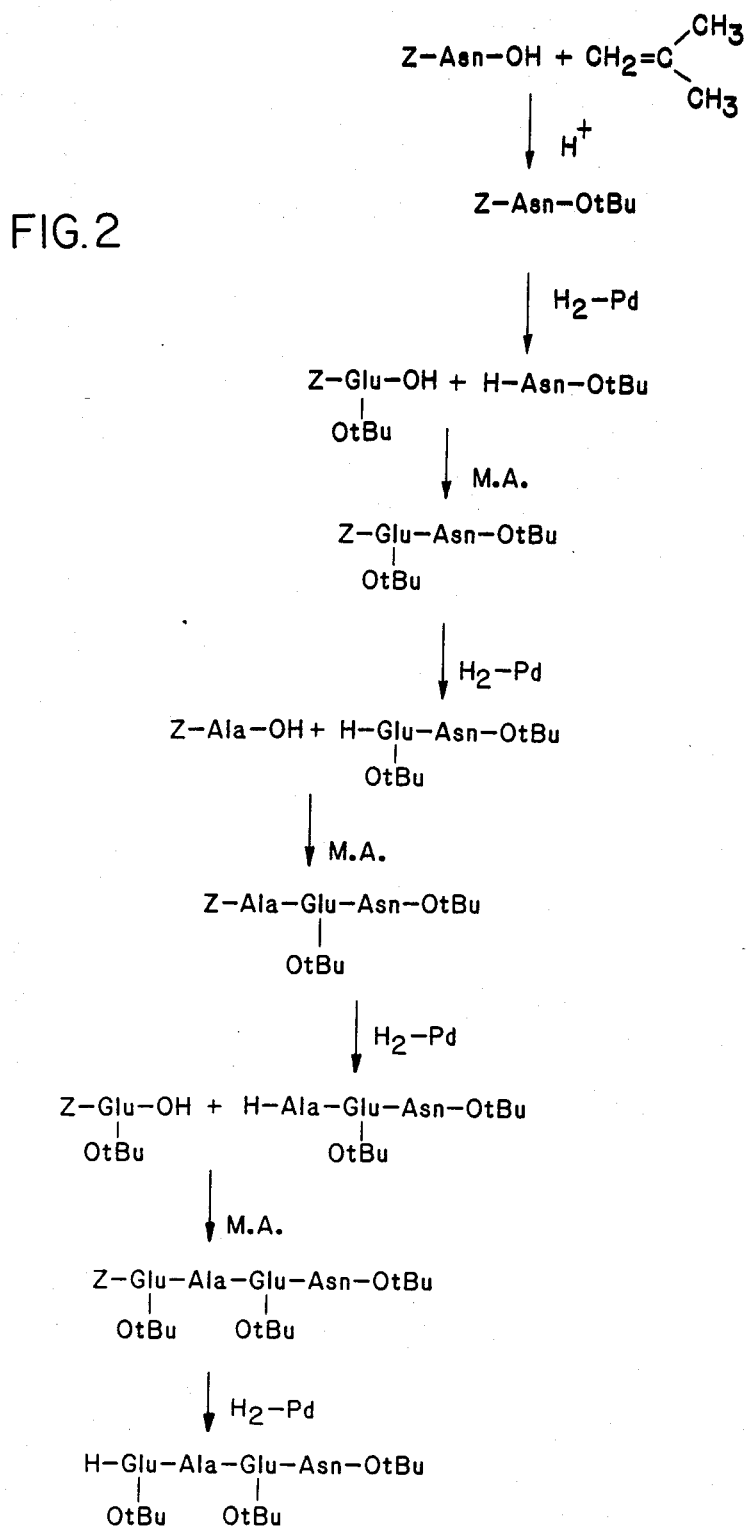
FIG. 2 sets forth the procedure used to synthesize fragment I.

As seen from the synthetic strategy set forth in FIG. 1 the procedure utilized for the synthesis of thymosin $\alpha_1$ and desacetylthymosin $\alpha_1$ required the synthesis of 7 fragments (I-VII). The synthetic approaches to the 7 fragments are outlined in Schemes 1-7 (FIGS. 2-8 respectively).

Fragment I was prepared by stepwise chain elongation using the mixed anhydride procedure at $-15°$ C. with careful temperature control. As seen in Scheme 1 of FIG. 2 mixed anhydride coupling (isobutylchloroformate) of Z-Glu(OtBu)-OH with H-Asn-OtBu provided Z-Glu(OtBu)-Asn-OtBu. Catalytic hydrogenation (10% Pd-C) of this compound cleaved the N-terminal protective group and the dipeptide was coupled to Z-Ala-OH using mixed anhydride coupling to give Z-Ala-Glu(OtBu)-Asn-OtBu. The N-terminal was again deprotected by catalytic hydrogenation and the tripeptide coupled with Z-Glu(OtBu)-OH to give the protected tetrapeptide Z-Glu(OtBu)-Ala-Glu(OtBu)-Asn-OtBu which is deblocked by catalytic hydrogenation to provide the desired tetrapeptide (I).

Figure 3:
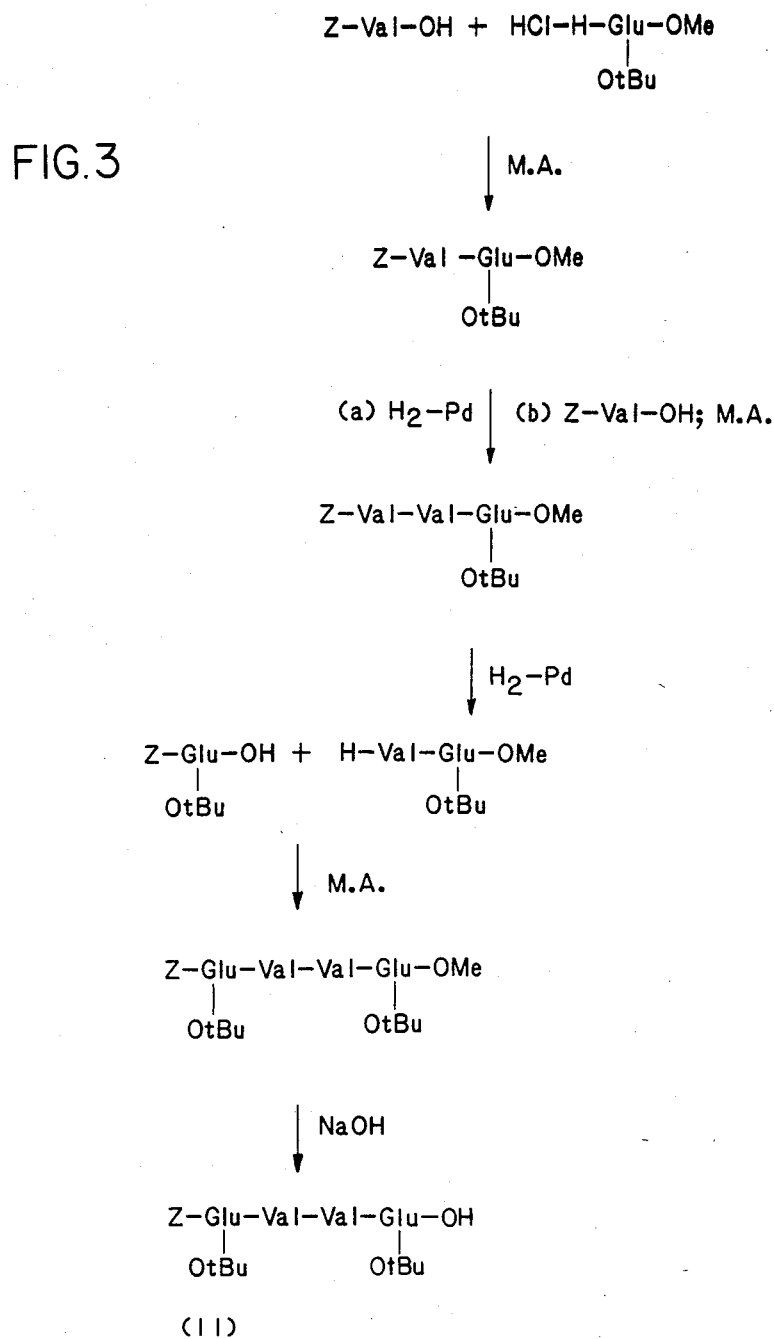
FIG. 3 sets forth the procedure used to synthesize fragment II.

The synthesis of fragment II is depicted in FIG. 3 by Scheme 2. Again all three coupling reactions were carried out by the mixed anhydride method. Thus HCL.H-Glu(OtBu)-OMe was converted to Z-Val-Glu(OtBu)-OMe, which after catalytic hydrogenation for 25 hours the resulting intermediate H-Val-Glu(OtBu)-OMe was immediately coupled (mixed anhydride) with Z-Val-OH. The resultant protected tripeptide Z-Val-Val-Glu(OtBu)-OMe was then catalytically hydrogenated to produce the corresponding N-terminal free peptide which was coupled (mixed anhydride) with Z-Glu(OtBu)-OH. The resulting protected tetrapeptide was then base saponified i.e., 1N NaOH in DMF to provide fragment II.

Figure 4:
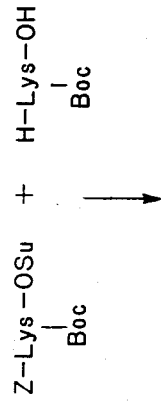
FIG. 4 sets forth the procedure used to synthesize fragment III.

In FIG. 4, the synthesis of fragment III by scheme 3 is shown. Coupling of Z-Lys(Boc)-OSu with H-Lys(Boc)-OH gave Z-Lys(Boc)-Lys(Boc)-OH as the DCHA salt. Conversion to the free acid using $H_2SO_4$ in ether was followed by catalytic hydrogenation (5% Pd-BaSO$_4$) and coupling with Z-Glu(OtBu)-OSu to yield the desired fragment III Z-Glu(OtBu)-Lys(Boc)-Lys(Boc)-OH.

Figure 5:
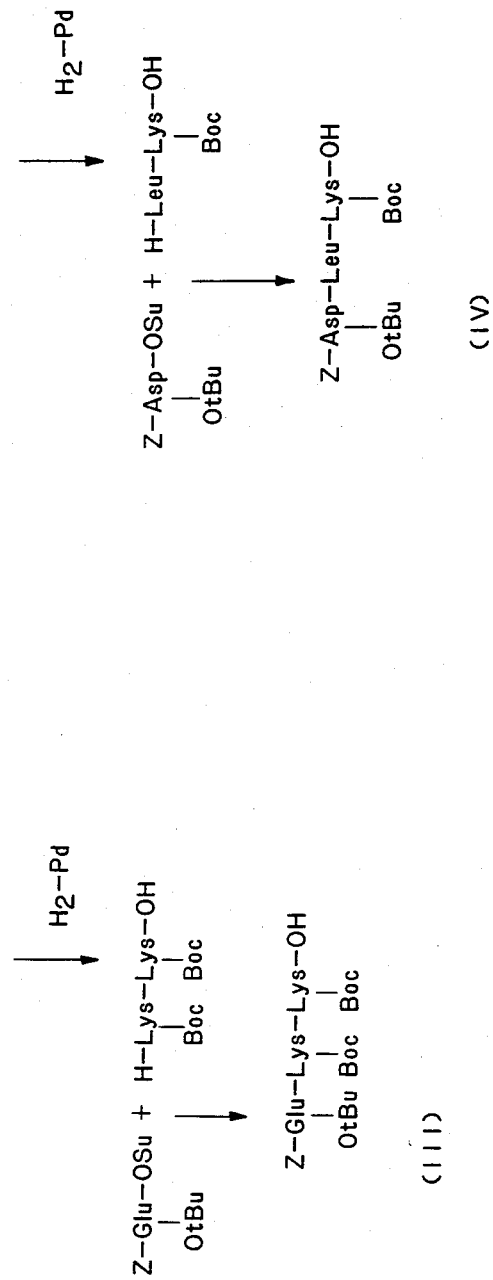
FIG. 5 sets forth the procedure used to synthesize fragment IV.

Scheme 4 shown in FIG. 5 describes the preparation of fragment IV. Conversion of Z-Leu-OH to Z-Leu- OSu and Z-Asp(OtBu)-OH to Z-Asp(OtBu)-OSu was carried out in a manner known per se using DCC and HOSU. Coupling of Z-Leu-OSu with H-Lys(Boc)-Oh provided Z-Leu-Lys(Boc)-OH as the DCHA salt. Conversion to the free amino terminus followed by catalytic hydrogenolysis (Pd-BaSO$_4$) gave H-Leu-Lys(Boc)-OH. Final coupling of H-Leu-Lys(Boc)-OH with Z-Asp(OtBu)-OSu gave Fragment IV.

FIG. 6 shows the procedure used for preparing Fragment V by means of scheme 5. Z-Lys(Boc)-OH was esterified with phenol and the amino terminal deblocked by catalytic hydrogenation over 10% Pd-C in the presence of TosOH to form H-Lys(Boc)-OC$_6$H$_5$·TosOH. After coupling (mixed anhydride) with Z-Thr(tBu)-OH the resulting dipeptide is catalytically deblocked and coupled with Z-Thr(tBu)-OH to provide the tripeptide Z-Thr(tBu)-Thr(tBu)-Lys(Boc)-OC$_6$H$_5$. After another cycle of catalytic deblocking and coupling with Z-Ile-OH (mixed anhydride), the resulting tetrapeptide ester is saponified with dilute, basic hydrogen peroxide to yield the desired fragment V, Z-Ile-Thr(tBu)-Thr(tBu)-Lys(Boc)-OH.

Figure 7:
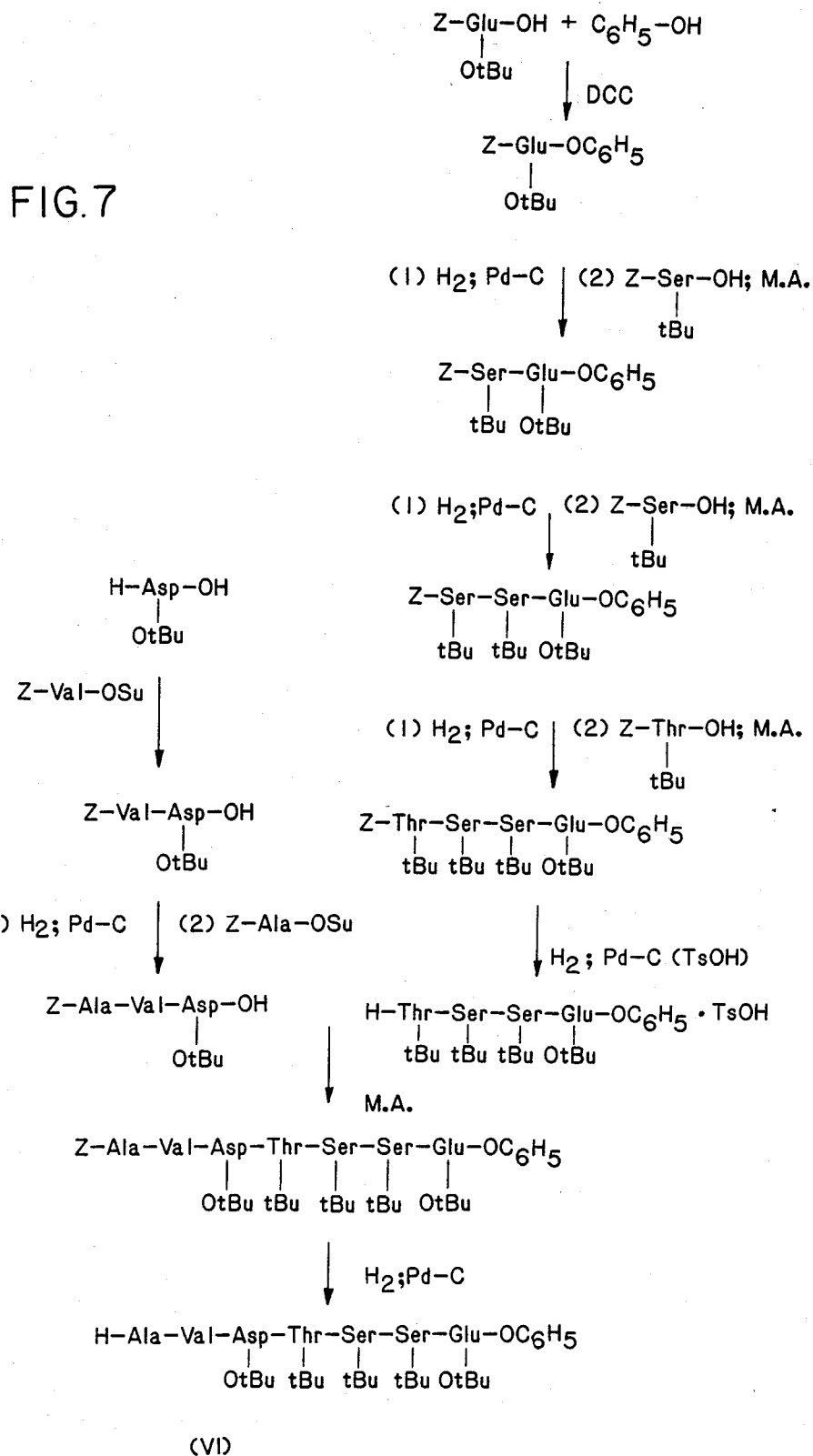
FIG. 7 sets forth the procedure used to synthesize fragment VI.

The synthesis of fragment VI by scheme 6 is shown in FIG. 7. The esterification of Z-Glu(OtBu)-OH with phenol is carried out under conventional conditions and the resulting phenyl ester, after catalytic (Pd-C) deblocking is coupled (mixed anhydride) with Z-Ser(tBu)-OH to provide the dipeptide Z-Ser(tBu)-Glu(OtBu)-OC$_6$H$_5$. Two additional cycles of deblocking and mixed anhydride coupling with Z-Ser(tBu)-OH and Z-Thr(tBu)-OH respectively provided the protected tetrapeptide Z-Thr(tBu)-Ser(tBu)-Ser(tBu)-Glu(OtBu)-OC$_6$H$_5$. Catalytic deprotection in the presence of TosOH gave the corresponding free amino terminus tetrapeptide as the tosyl salt, which upon mixed anhydride coupling with Z-Ala-Val-Asp(OtBu)-OH and catalytic deblocking provided the desired heptapeptide fragment VI.

As further seen in FIG. 7 the tripeptide coupling partner is built up by reacting Z-Val-OSu with H-Asp(OtBu)-OH, deblocking the resulting dipeptide by catalytic hydrogenation with Pd-C and then coupling with Z-Ala-OSu.

Construction of the final fragment, Fragment VII, is set forth in scheme 7 shown in FIG. 8. Mixed anhydride coupling of Z-Asp(OtBu)-OH with H-Ala-OBzl produced the protected dipeptide which was deblocked by catalytic hydrogenation with Pd-C in the presence of TosOH. The resulting deblocked peptide in the form of the tosyl salt with then coupled to Z-Ser(tBu)-OSu to provide the protected tripeptide Z-Ser(tBu)-Asp(OtBu)-Ala-OH. After deblocking by catalytic hydrogenation the resulting tripeptide can be treated with acetic anhydride to provide the blocked N-terminal acetyl tripeptide. This blocked tripeptide, Ac-Ser(tBu)-Asp(OtBu)-Ala-OH, is then converted to the corresponding succinimide ester to thereby yield the desired Fragment VII.

In the case of the preparation of deascetyl thymosin $\alpha_1$, the corresponding equivalent Fragment VII consists of Boc-Ser(tBu)-Asp(OtBu)-Ala-OSu.

The present invention is more clearly understood by reference to the following Examples which serve to illustrate but not limit the instant invention.

EXAMPLES

Materials

All amino acid derivatives were of the L-configuration unless otherwise stated. Dimethylformamide (reagent grade, Matheson Colemen and Bell) was distilled from ninhydrin at reduced pressure and stored over molecular sieve. Tetrahydrofuran (reagent grade, Matheson Coleman and Bell) was distilled from LiAlH$_4$. Trifluoroacetic acid and N-Methylmorpholine (Chemical Dynamics) were sequalog grade purity. Trifluoroethanol (Aldrich Chemical Co.) was distilled at atmospheric pressure prior to use. Dimethylsulfoxide (distilled in glass) and pyridine (distilled in glass) were purchased from Burdick and Jackson. Hydroxybenzotriazole and triethylamine (sequenal grade purity) were purchased from Pierce Chemical Co. The catalysts for hydrogenation were purchased from the Englehard Co. Catalytic hydrogenations were carried out in a Vibromixer apparatus as previously described, Meienhofer, Chima 16, 385 (1962). All other solvents were of reagent grade and used without further purification.

Methods

Amino acid analyses were performed on the Beckman Model 121M Amino Acid Analyzer. The free peptides were hydrolyzed in 6M HCl (Pierce Chemical Co.) in sealed, evacuated tubes for 24 h at 110° C. Hydrolysis time was increased by 72 h for the peptides which incorporated the -Val-Val-residue as indicated by (a). TLC was carried out on silica gel G plates (Analtech, Inc.) and developed with chlorine-TDM. Typically, 2 mg of sample was dissolved in 150 $\mu$l of solvent and 3 $\mu$l (50 $\mu$g) applied to the tlc plate.

Melting points were determined on the Hoover apparatus (with correction) or on a Reichert hot stage apparatus (without correction). Infra-red and nmr spectra were measured and found to be compatible for all new products synthesized. Optical rotations were measured in a jacketed 1-dm cell on a Perkin Elmer Moddel 141 Polarimeter. Electrophoresis was carried out on the Camag HVE apparatus using S&S 2040-B paper and silica gel G plates (see above) and developed with ninhydrin.

The CD spectrum was measured on a Jasco ORD-UV/5 spectro-polarimeter at ambient temperature in 0.05M phosphate buffer at pH 7.4 using a concentration of $2 \times 10^{-4}$M and path lengths of 0.001 dm to 0.10 dm. The spectrum was qualitatively similar to that reported for thymosin $\alpha_1$. The nmr spectra of the 2 peptide fragments, 8 and 12, were measured on a Varian XL-100 Spectrometer. The nmr spectrum of thymosin $\alpha_1$ was measured on a Varian XL-200 Spectrometer. Peptide mapping was carried out by digesting thymosin $\alpha_1$ with trypsin-TPCK at pH 8.0. The fragment migration patterns on tlc plates (see above) were found to be identical to the reference standard. Isoelectric focusing was carried out using a DC LKB-2103 power supply and LKB 2177 multiphor. The protein precipitin bands and coomasie staining was identical to the reference standard.

High performance liquid chromatography was performed on an LDC Constametric IIG equipped with a gradient master and Spectromonitor III UV detector (206 nm). A Waters Bondapack C$_{18}$ with a pre-column of Copell ODS pellicular packing (Whatman) was used. The column was equilibrated with 8% CH$_3$CN in H$_2$O containing 0.022% TFA. The sample in H₂O (~1 μg/μL) was adjusted to pH ~8 with 0.1N NH₄OH and applied onto the column and eluted with 0.022T% TFA-H₂O and a linear gradient of 0.022% TFA-CH₃CN was introduced to bring the CH₃CN concentration to 22% over a period of 30 min (flow rate 2 mL/min.).

EXAMPLE 1

N-Benzlyloxycarbonyl-γ-t-butyl-L-glutamyl-L-valyl-L-valyl-γ-t-butyl-L-glutamic acid, II, 1

A solution of Z-Glu(OtBu)-Val-Val-Glu(OtBu)-OMe (46.5 g, 63.3 mmol) in DMF (550 mL) was treated with 1N NaOH (79.2 mL, 79.2 mmol, 1.25 eq.) and stirred magnetically for 3 h at 25°. It was cooled in an ice-bath and 1N HCl (190 mL) added followed by 1.25 L H₂O. The suspension was stirred for 2 h at 25° and the product collected by filtration, washed with 1 L H₂O and dried in vacuo. Yield: 41.9 g (91.8%). An analytical sample was recrystallized from MeOH-H₂O; mp 193°–196°; $[\alpha]_D^{25}$ −51.66° (c 1, MeOH); $R_f$ 0.34 (CHCl₃:MeOH:AcOH; 80-5-1). Anal. calc. for $C_{36}H_{56}N_4O_{11}$ (720.86): C, 59.98; H, 7.83; N, 7.77. Found: C, 59.91; H, 7.75; N, 7.85.

EXAMPLE 2

Z-Glu(OtBu)-Val-Val-Glu(OtBu)-Glu(OtBu)-Ala-Glu(OtBu)-Asn-OtBu, 2

A solution of Z-Glu(OtBu)-Val-Val-Glu(OtBu)-OH (1, II, 35.5 g, 0.049 mol) and H-Glu(OtBu)-Ala-Glu(OtBu)-Asn-OtBu (I, 31.5 g, 0.05 mol) in DMF (850 mL) was cooled to 0° and HOBt (22.7 g, 0.148 mol, 3 eq.) was added with mechanical stirring. DCC (15.3 g, 0.074 mol, 1.65 eq.) was added and the pH was adjusted to 7.5–8.0 by addition of N-methylmorpholine (~15 mL). Stirring proceeded for 1 hr at 0° and 23 hr at 25°, filtered and the filtrate poured into H₂O (8 L) and stirred for 1.5 h. The product was collected by filtration, washed with H₂O (8 L), dried and washed with MeOH (4×250 mL) and dried in vacuo to give 46.8 g. Recrystallization from MeOH gave a white solid. Yield: 39.6 g (60%); mp 244°–245°, $[\alpha]_D^{25}$ −20.65° (c 0.5, DMSO); $R_f$ 0.35 (CHCl₃:MeOH:AcOH; 80-5-1). Amino Acid Anal. (6M HCl, 110°, 24 h): Asp (0.96); Glu (4.06); Ala (0.99); Val (1.78).[a] Anal. calc. for $C_{65}H_{105}N_9O_{20}$ (1332.6): C, 58.59; H, 7.94; N, 9.45. Found: C, 58.42; H, 7.85; N, 9.72.

[a] 72 hour hydrolysate for Val.

EXAMPLE 3

H-Glu(OtBu)-Val-Val-Glu(OtBu)-Glu(OtBu)-Ala-Glu(OtBu)-Asn-OtBu, 3,

A solution of Z-Glu(OtBu)-Val-Val-Glu(OtBu)-Glu(OtBu)-Ala-Glu(OtBu)-Asn-OtBu (Ro 22-4311/001, 42.6 g; 32.0 mmol) in DMF (650 mL) containing 10% Pd-BaSO₄ (15.0 g) was hydrogenated in a Vibromixer apparatus for 3 h. The reaction mixture was filtered through a bed of celite which was washed with DMF (5×250 mL). The combined filtrate was evaporated to 600 mL and DMSO (300 mL) added. The resultant solution was used for the next stage of synthesis. A portion was evaporated to dryness, taken up in MeOH and precipitated with Et₂O. The resultant gel was filtered, washed with Et₂O and dried in vacuo; mp 246°–249° dec; $[\alpha]_D^{25}$ −18.78° (c 1, DMF); $R_f$ 0.78 (n-BuOH:AcOH:Pyr:H₂O; 1-1-1-1). Anal. calc. for $C_{57}H_{99}N_9O_{18}$ (1198.46): C, 57.13; H, 8.33; N, 10.52. Found: C, 56.83; H, 8.32; N, 10.39.

EXAMPLE 4

Z-Glu(OtBu)-Lys(Boc)-Lys(Boc)-Glu(OtBu)-Val-Val-Glu(OtBu)-Glu(OtBu)-Ala-Glu(OtBu)-Asn-OtBu, 4

The DMF:DMSO-containing solution of H-Glu(OtBu)-Val-Val-Glu(OtBu)-Glu(OtBu)-Ala-Glu(OtBu)-Asn-OtBu (~32 mmol) from Example 3 was combined with Z-Glu(OtBu)-Lys(Boc)-Lys(Boc)-OH, III, Ro 22-4541 (36.8 g, 46 mmol, 1.44 eq.) and HOBt (14.7 g, 96 mmol, 3 eq.) added and the solution cooled to 0°. DCC (10.9 g, 52 mmol, 1.65 eq.) was added to the cold stirring (mechanical) reaction mixture and the pH was maintained at 7.5–8.0 by addition of N-methylmorpholine (21 mL). Stirring proceeded for 2 h at 0° and 21 h at 25°. The resultant gelatenous reaction mixture was poured into H₂O (9.0 L) and stirred for 4 h. The product was collected by filtration, washed with H₂O (8×500 mL), dried and washed with MeOH using the centrifuge to separate the 2 phases. When all the dicyclohexylurea was removed the product was combined and dried in vacuo to give 45.22 g (71.5%); mp 312° dec; $[\alpha]_D^{25}$ −18.20° (c 1, DMSO); $[\alpha]_D^{25}$ −13.27° (c 1, TFE); $R_f$ 0.81 (n-BuOH:AcOH:Pyr:H₂O; 15-3-10-12); $R_f$ 0.52 (CHCl₃:MeOH:AcOH; 85-10-5). Amino Acid Anal. (6M HCl, 110°, 24 h): Asp(1.04); Glu(5.04); Ala(1.02); Lys(1.90); Val (1.67).[a] Anal. calc. for $C_{96}H_{160}N_{14}O_{29}$ (1974.4): C, 58.40; H, 8.17; N, 9.93. Found: C, 57.84; H, 8.28; N, 9.94.

[a] 72 hour hydrolysate for Val.

EXAMPLE 5

H-Glu(OtBu)-Lys(Boc)-Lys(Boc)-Glu(OtBu)-Val-Val-Glu(OtBu)-Glu(OtBu)-Ala-Glu(OtBu)-Asn-OtBu, 5

A solution of Z-Glu(OtBu)-Lys(Boc)-Lys(Boc)-Glu(OtBu)-Val-Val-Glu(OtBu)-Glu(OtBu)-Ala-Glu(OtBu)-Asn-OtBu (45.0 g, 23 mmol) in TFE (1.1 L) containing 10% Pd-BaSO₄ (15 g) was hydrogenated in a Vibromixer apparatus for 3 h. The reaction mixture was filtered through celite which was washed with TFE (3×100 mL). The combined filtrate was evaporated to dryness and taken up in DMF:DMSO (1300 mL:650 mL) for use in the next stage of synthesis. A portion of the residue was precipitated from TFE-H₂O, filtered and dried in vacuo; mp 326°–327°; $[\alpha]_D^{25}$ −17.65° (c 1, DMSO); $R_f$ 0.73 (n-BuOH:AcOH:EtOAc:H₂O; 1-1-1-1). Anal calc. for $C_{88}H_{154}N_{14}O_{27} \cdot H_2O$ (1876.27): C, 56.33; H, 8.49; N, 10.45. Found: C, 56.40; H, 8.69; N, 10.55.

EXAMPLE 6

Z-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu, 6,

The DMF:DMSO-containing solution of H-Glu(OtBu)-Lys(Boc)-Lys(Boc)-Glu(OtBu)-Val-Val-Glu(OtBu)-Glu(OtBu)-Ala-Glu(OtBu)-Asn-OtBu (~23 mmol) from Example 5 was combined with Z-Asp(OtBu)-Leu-Lys(Boc)-OH, IV, (18.6 g, 28.0 mmol, 1.2 eq.) and HOBt (10.62 g, 69.0 mmol, 3.0 eq.) added and the solution cooled to 0°. DCC (7.87 g, 38.0 mmol, 1.65 eq.) was added to the cold stirring (mechanical) reaction mixture and the pH was maintained at 7.5–8.0 by addition of N-methylmorpholine (~17 mL). Stirring proceeded for 1 h at 0° and 23 h at 25°. The resultant reaction mixture was poured into H₂O (10 L) and stirred for 1.5 h. The product was collected by filtration, washed with H₂O (5 L), dried and washed with MeOH using the centrifuge to separate the 2 layers. When all the dicyclohexylurea was removed the product was pooled and dried in vacuo to give 44.56 g (77.9%); mp >330°; $[\alpha]_D^{25}$ −11.56° (c 1, TFE); $R_f$ 0.16 (CHCl₃:MeOH:AcOH; 80-5-1); $R_f$ 0.36 (CHCl₃:MeOH:TFE:AcOH; 85-10-2.5-1). Amino Acid Anal. (6M, HCl, 110°, 72 h): Asp (1.86); Glu (5.21); Ala (1.09); Val (1.90);[a] Leu (1.08); Lys (2.86). Anal calc. for C₁₂₁H₂₀₄N₁₈O₃₆ (2487.05): C, 58.43; H, 8.27; N, 10.13. Found: C, 57.96; H, 8.08; N, 10.16.

[a]72 hour hydrolysate for Val.

EXAMPLE 7

H-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu, 7,

A solution of Z-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu (35.56 g, 14.22 mmol) in TFE (720 mL) containing 5% Pd-BaSO₄ (11.8 g) was hydrogenated in a Vibromixer apparatus for 4 h. The reaction mixture was filtered through celite and evaporated to near dryness and precipitated with H₂O (2 L). The product was collected by filtration and dried in vacuo.

Yield: 32.74 g (95.7%); mp >320° $[\alpha]_D^{25}$ −6.54° (c 1, TFE); $R_f$ 0.42 (CHCl₃:MeOH:AcOH; 85-10-5). Anal. calc. for C₁₁₃H₁₉₈N₁₈O₃₄.3H₂O (2406.9): C, 56.39; H, 8.54; N, 10.48. Found: C, 56.32; H, 8.28; N, 10.55.

EXAMPLE 8

Z-Ile-Thr(tBu)-Thr(tBu)-Lys(Bos)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu, 8,

A solution of H-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu.3H₂O (16.72 g, 6.95 mmol) in DMF:DMSO (654:327 mL) as combined with Z-Ile-Thr(tBu)-Thr(tBu)-Lys(Boc)-OH, V, Ro 22-5604/001 (8.76 g, 10.4 mmol, 1.5 eq.) and HOBt (3.19 g, 20.9 mmol, 3 eq.) added and the solution cooled to 0°. DCC (2.37 g, 11.5 mmol, 1.65 eq.) was added to the cold stirring (mechanical) reaction mixture and the pH was maintained at 7.5-8.0 by addition of N-methylmorpholine (~4.7 mL). Stirring proceeded for 1 h at 0° and 48 h at 25°. The reaction mixture was cooled to 0° and a second coupling carried out as follows: Z-Ile-Thr(tBu)-Thr(tBu)-Lys(Boc)-OH (2.92 g, 3.47 mmol, 0.5 eq.), HOBt (1.06 g, 6.95 mmol, 1 eq.) and DCC (0.86 g, 4.17 mmol, 0.6 eq.) added and stirring proceeded at 0° for 1 h and at 25° for 17 h. The reaction mixture was poured into H₂O (5 L), stirred, filtered and washed with H₂O (3×1 L), MeOH (3×500 mL), DMSO (3×500 mL) and MeOH (2×500 mL). The product was dried in vacuo. Yield: 15.95 g (73.2%); mp 347°-349° dec; $R_f$ 0.21 (CHCl₃:MeOH:AcOH; 80-5-1); $R_f$ 0.56 (CHCl₃:MeOH:AcOH; 85-10-5); $R_f$ 0.46 (CHCl₃:MeOH:TFE:AcOH; 85-10-2.5-1); $[\alpha]_D^{25}$ −9.17° (c 0.1, TFE). Amino Acid Anal. (6M HCl, 110°, 24 h): Asp (2.02); Thr (1.70); Glu(5.12); Ala(1.12); Val(2.09);[a] Ile(0.88); Leu(1.09); Lys(3.87). Anal. calc. for C₁₅₄H₂₆₅N₂₃O₄₄.3H₂O (3197.0): C, 57.86; H, 8.54; N, 10.08; H₂O, 1.69. Found: C, 57.68; H, 8.45; N, 10.03; H₂O, 1.57.

[a]72 hour hydrolysate

EXAMPLE 9

H-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu, 9,

A solution of Z-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu (32.24 g, 10.25 mmol) in TFE (700 mL) containing 10% Pd-C (16.0 g) was hydrogenated in a Vibromixer apparatus for 3 h and a fresh charge of 10% Pd-C (8.0 g) added and the hydrogenation continued for 3 h more. The reaction mixture was filtered through celite which was washed with TFE (110 mL) and the filtrate and washings combined for use in the next stage of synthesis. A portion was purified by chromatography on silica gel 60 using a LOBAR-prepacked column (Size C). In a typical experiment 4 g of crude material in TFE was loaded onto the column and a sequential step gradient was employed starting with CHCl₃:MeOH:TFE:AcOH (96.5-0-2.5-1) and ending with CHCl₃:MeOH:TFE:AcOH (0-96.5-2.5-1). The product was pooled and evaporated to 1.9 g of analytically pure product; $[\alpha]_D^{25}$ −7.01° (c 0.3, TFE); $R_f$ 0.36 (CHCl₃:MeOH:TFE:AcOH; 85-10-2.5-1); mp 336°-338° dec. Amino Acid Anal. (6M HCl, 110°, 24 h): Asp (1.96); Thr (2.00); Glu (5.35); Ala (1.03); Val (2.00); Leu (0.97); Ile (1.11); Lys (3.86). Anal. calc. for C₁₄₆H₂₅₉N₂₃O₄₂ (3008.8): C, 58.28; H, 8.68; N, 10.71. Found: C, 58.33; H, 8.38; N, 10.90.

EXAMPLE 10

Ac-Ser(tBu)-Asp(OtBu)-Ala-OSu, VII, 10,

A solution of Ac-Ser(tBu)-Asp(OtBu)-Ala-OH (24.7 g, 55.4 mmol) in dry THF (526 mL) was treated with HOSu (9.55 g, 83.1 mmol, 1.5 eq.) and cooled to 0°. To the cold stirring (mechanical) solution DCC (17.14 g, 83.1 mmol, 1.5 eq.) was added portionwise and stirring proceeded at 0° for 30 min at 25° for 5 h. The reaction mixture was filtered and the filtrate evaporated to dryness and crystallized from isopropanol (250 mL). Yield: 23.2 g (77.2%); mp 155°-157°; $[\alpha]_D^{25}$ −41.48° (c 1, MeOH); $R_f$ 0.54 (CHCl₃:MeOH:AcOH; 80-5-1). Anal. calc. for C₂₄H₃₈N₄O₁₀ (542.58): C, 53.13; H, 7.06; N, 10.33. Found: C, 53.21; H, 6.85; N, 10.29.

EXAMPLE 11

H-Ala-Val-Asp(OtBu)-Thr(tBu)-Ser(tBu)-Ser(tBu)-Glu(OtBu)-OC₆H₅, VI, 11

A solution of Z-Ala-Val-Asp(OtBu)-Thr(tBu)-Ser(tBu)-Ser(tBu)-Glu(OtBu)-OC₆H₅ (20.16 g; 16.8 mmol) in DMF (400 mL) was hydrogenated with 5% Pd-BaSO₄ (10 g) for 2 h in a Vibromixer apparatus. The reaction mixture was filtered through celite which was washed with additional DMF (228 mL). The combined filtrate was used directly in the next stage of synthesis. A portion of the material was precipitated by addition of H₂O, filtered and dried in vacuo; mp >275°; $[\alpha]_D^{25}$ −9.28° (c 1, TFE); $R_f$ 0.77 (n-BuOH:AcOH:Pyr:H₂O; 4-7-1-1); $R_f$ 0.65 (n-BuOH:H₂O:AcOH:EtOAc; 1-1-1-1). Anal. calc. for C₅₃H₈₉N₇O₁₅.H₂O (1082.36): C, 58.82; H, 8.48; N, 9.06. Found: C, 59.11; H, 8.56; N, 9.23.

EXAMPLE 12

Ac-Ser(tBu)-Asp(OtBu)-Ala-Ala-Val-Asp(OtBu)-Thr(tBu)-Ser(tBu)-Ser(tBu)-Glu(OtBu)-OC$_6$H$_5$, 12

The DMF-containing solution of H-Ala-Val-Asp(OtBu)-Thr(tBu)-Ser(tBu)-Ser(tBu)-Glu(OtBu)-OC$_6$H$_5$ (~16.8 mmol) from the preceeding step was cooled to 0° and Ac-Ser(tBu)-Asp(OtBu)-Ala-OSu, VII, (10.92 g, 20.16 mm, 1.2 eq.) added. Stirring proceeded at 0° for 30 min and 25° for 17 h while the pH was maintained at ~8 by addition of Et$_3$N. Water (2.4 L) was added with stirring and the product was collected by filtration and dried in vacuo. The solid was crushed and washed with CH$_3$OH (3×200 mL) and dried in vacuo. Yield: 23.0 g (91.7%); mp 255°–256°; R$_f$ 0.48 (CHCl$_3$:CH$_3$OH:AcOH; 80-5-1); $[\alpha]_D^{25}$ −25.60° (c 1, TFE). Anal. calc. for C$_{73}$H$_{122}$N$_{10}$O$_{22}$ (1491.86): C, 58.77; H, 8.24; N, 9.39. Found: C, 58.54; H, 8.23; N, 9.43.

EXAMPLE 13

Ac-Ser(tBu)-Asp(OtBu)-Ala-Ala-Val-Asp(OtBu)-Thr(tBu)-Ser(tBu)-Ser(tBu)-Glu(OtBu)-OH, 13

A solution of Ac-Ser(tBu)-Asp(OtBu)-Ala-Ala-Val-Asp(OtBu)-Thr(tBu)-Ser(tBu)-Ser(tBu)-Glu(OtBu)-OC$_6$H$_5$ (22.73 g, 15.2 mmol) in TFE: H$_2$O (270 mL: 20 mL) was treated with 3% H$_2$O$_2$ (15.5 ml, 15.2 mmol, 1 eq.) with stirring (magnetic). The reaction mixture was adjusted to pH 10.5 by addition of 1N NaOH and maintained at pH 10.5 over a period of 3 h by addition of 1N NaOH (triggered by an autotitrator). The reaction mixture was adjusted to pH 3 (1N HCl), filtered and the solid washed with H$_2$O (200 mL) and dried in vacuo. Yield: 21.85 g (98.8%); mp >245° dec; $[\alpha]_D^{25}$ −16.31° (c 0.4, TFE); R$_f$ 0.67 (CHCl$_3$:MeOH:AcOH; 85-10-5). Amino Acid Anal. (6M HCl, 110°, 24 h): Asp (1.99); Thr (0.96); Ser (2.83); Glu (1.02); Ala (1.99); Val (1.01). Anal. calc. for C$_{67}$H$_{118}$N$_{10}$O$_{22}$·2H$_2$O (1451.79): C, 55.43; H, 8.19; N, 9.65. Found: C, 55.24; H, 8.24; N, 9.56.

EXAMPLE 14

Ac-Ser(tBu)-Asp(OtBu)-Ala-Ala-Val-Asp(OtBu)-Thr(tBu)-Ser(tBu)-Ser(tBu)-Glu(OtBu)-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu, 14

A solution of H-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu (8.822 g, 2.932 mmol) in TFE (230 ml) and Ac-Ser(tBu)-Asp(OtBu)-Ala-Ala-Val-Asp(OtBu)-Thr(tBu)-Ser(tBu)-Ser(tBu)-Glu(OtBu)-OH (10.82 g, 7.66 mmol, 2.6 eq.) was treated with HOBt (7.86 g, 51.3 mmol, 10 eq.) and cooled to 0°. DCC (4.49 g, 16.1 mmol, 5.5 eq.) was added to the cold stirring solution followed by the addition of N-methyl-morpholine (5.25 mL, 46.9 mmol, 16 eq.). Stirring proceeded for 1 h at 0° and 23 h at 25°. The reaction mixture was poured into H$_2$O (5 L) and the product was filtered, washed with H$_2$O (3×500 mL), MeOH (3×250 mL), DMSO (3×250 mL) and MeOH (3×250 mL) and dried in vacuo. Yield: 14.985 g. TLC shows the presence of some starting materials and a new major spot corresponding to product: R$_f$ 0.56 (CHCl$_3$:MeOH:AcOH; 85-10-5); R$_f$ 0.56 (CHCl$_3$:MeOH:TFE:AcOH; 85-10-2.5-1). This material can be used directly in the following deprotection step or alternatively after purification by column chromatography as follows.

5.0 g (2.83 g maximum content of 28 mer) of crude fully protected 28 mer in TFE (25 mL) was applied onto a 64×6.5 cm column packed with Merck Silica Gel (775 g) and equilibrated with CH$_2$Cl$_2$ (2.5% in TFE). The column was eluted (gravity) with CH$_2$Cl$_2$ (2.5% in TFE) for 50 fractions (20 mL/fraction); CH$_2$Cl$_2$:MeOH (95-5) (2.5% in TFE) for 68 fractions; CH$_2$Cl$_2$:MeOH (90:10) (2.5% in TFE) for 127 fractions and CH$_2$Cl$_2$:MeOH (80:20) (2.5% in TFE) for 212 fractions. Fractions 251–360 were pooled, evaporated to dryness and precipitated from TFE-H$_2$O to give 532 mg (19%) of protected 28 mer; mp >300°; R$_f$ 0.40 (CHCl$_3$:MeOH:AcOH; 80-10-5); R$_f$ 0.40 (CHCl$_3$:MeOH:AcOH; 80-10-0.5); R$_f$ 0.36 (CHCl$_3$:MeOH:TFE:AcOH; 85-10-2.5-1). Amino Acid Anal. (6N HCl; 110°; 24 h): Asp, 4.0; Thr, 3.0; Ser, 3.1; Glu, 5.8; Ala, 3.2; Val, 2.9[a]; Ile, 0.9; Leu, 1.1; Lys, 4.0. Anal. Calcd. for C$_{213}$H$_{375}$N$_{33}$O$_{63}$ (MW 4406.5): C, 58.05; H, 8.58; N, 10.49. Found: C, 57.58; H, 8.56; N, 10.54.

[a] 72 hour hydrolysate

EXAMPLE 15

Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH, 15

Thymosin α$_1$

The crude fully protected 28-peptide, 14 (14.985 g) was deprotected with TFA:CH$_2$Cl$_2$ (65 mL: 65 mL) in 6 separate lots under N$_2$ for 2.5 h at 25°. The reaction mixtures were filtered and the filtrate poured into ether (1.6 L total volume) and the resultant precipitate washed with ether (2×200 mL) and dried in vacuo to give 10.274 g of crude thymosin α$_1$.

A 2.578 g portion of the crude thymosin α$_1$ was taken up in H$_2$O (10 mL) and the pH adjusted to 8.0 (conc. NH$_4$OH), filtered through a 0.45µ millipore filter and applied onto a Whatman Partisil-10 Magnum 20 ODS-3 (2×50 cm column) containing C$_{18}$ reverse phase silica gel (10 µm) which was previously equilibrated with Pyridine (3%): Acetic acid (3%). The elution was carried out (flow rate 8 mL/min) using a Constametric Series LDC unit) with Pyridine (3%): Acetic acid (3%) for 60 min and followed by gradient elution with 0 to 14% acetonitrile for 60 minutes and finally eluted with pyridine (3%): Acetic acid (3%): acetonitrile (14%) for 6 hours. The column was finally stripped with pyridine (3%): Acetic acid (3%): acetonitrile (gradient from 14 to 90%). Factions were collected at 2 min intervals and monitoring was carried out simultaneously with o-phthalaldehyde using a Gilson excitation-fluorescence monitor (λ=455 nm). Appropriate fractions were pooled and lyophilized:

| Fractions | Amount | |
|---|---|---|
| 1–42 | 2.14 g | |
| 43–45 | 40 mg | |
| 46–66 | 220 mg | ← PURE THYMOSIN α$_1$ |
| 67–82 | 40 mg | |
| strip | 420 mg | (pyridine:acetic acid (8-3) in 1:1 CH$_3$CN—IprOH) |

The remaining 7.696 g of crude thymosin α$_1$ was purified in 5 lots by preparative HPLC as described above. A total of 1.170 g of pure thymosin α$_1$ was prepared by this method. Theoretical yield of thymosin α₁ (based on 2.932 mmol of H-18-peptide)=9.114 g; % yield=12.84%.

EXAMPLE 16

Bos-Ser(tBu)-Asp(OtBu)-Ala-OSu

A solution of Boc-Ser(tBu)-Asp(OtBu)-Ala-OH.CHA (1.205 g, 2.0 mmol) was extracted with a mixture of EtOAc: 0.5N H₂SO₄ (10 mL-10 mL). The organic layer was retained, washed with saturated NaCl, dried (MgSO₄) and evaporated in vacuo. The resultant free acid in EtOAc:dioxane (5 mL-10 mL) was treated with HOSu (230 mg, 2.0 mmol, 1 eq) and cooled to 0°. To the cold stirring solution DCC (412 mg, 2.0 mm, 1 eq) was added portionwise and stirring proceeded at 0° for 1 hr and at 25° for 48 hr. The reaction mixture was filtered and the filtrate evaporated to dryness and crystallized from isopropanol-petroleum ether. Yield: 631 mg (52.5%); mp 129°-136°; [α]$_D^{25}$ −32.74° (c 1, MeOH); R$_f$ 0.86 (CHCl₃:MeOH:AcOH; 85-10-5); R$_f$ 0.79 (CHCl₃:MeOH:AcOH; 80-5-2). Anal. calc. for C₂₇H₄₄N₄O₁₁ (600.67): C, 53.99; H, 7.38; N, 9.33. Found C, 53.85; H, 7.50; N, 9.29.

EXAMPLE 17

Boc-Ser(tBu)-Asp(OtBu)-Ala-Ala-Val-Asp(OtBu)-Thr(tBu)-Ser(tBu)-Ser(tBu)-Glu(OtBu)-OC₆H₅

A solution of H-Ala-Val-Asp(OtBu)-Thr(tBu)-Ser(tBu)-Ser(tBu)-Glu(OtBu)-OC₆H₅ 0.708 mmol) in DMF (34 mL) was cooled to 0° and Boc-Ser(tBu)-Asp(OtBu)-Ala-OSu 510 mg, 0.85 mmol, 1.2 eq) added. Stirring proceeded at 0° for 30 min and 25° for 17 h while the pH was maintained at ~8 by addition of Et₃N. Water (150 mL) was added with stirring and the product was collected by filtration and dried in vacuo. The solid was washed with CH₃OH (2×20 mL) and dried in vacuo. Yield: 586 mg (53.3%); mp >250°; [α]$_D^{25}$ −23.06° (c 1, TFE); R$_f$ 0.51 (CHCl₃:MeOH:AcOH; 80-2-0.4); R$_f$ 0.72 (CHCl₃:MeOH:AcOH; 80-5-2). Anal. calc. for C₇₆H₁₃₁N₁₀O₂₃ (1552.93): C, 58.78; H, 8.50; N, 9.01. Found: C, 58.65; H, 8.32; N, 8.93.

EXAMPLE 18

Boc-Ser(tBu)-Asp(OtBu)-Ala-Val-Val-Asp(OtBu)-Thr(tBu)-Ser(tBu)-Ser(tBu)-Glu(OtBu)-OH

A solution of Boc-Ser(tBu)-Asp(OtBu)-Ala-Val-Val-Asp(OtBu)-Thr(tBu)-Ser(tBu)-Ser(tBu)-Glu(OtBu)-OC₆H₅ (452 mg, 0.29 mmol) in TFE:H₂O (5.2-0.4 mL) was treated with 3% H₂O₂ (0.31 mL, 0.30 mmol, 1.0 eq) with stirring (magnetic). The reaction mixture was adjusted to pH 10.5 by addition of 1N NaOH (triggered by an autotitrator) and maintained at that pH for 3 h. The reaction mixture was adjusted to pH ~1 with 1M HCl, refrigerated, filtered and washed with H₂O and CH₃OH and dried in vacuo. Yield: 423 mg (98.4%); mp ~245° dec; [α]$_D^{25}$ −13.28° (c 1, TFE); R$_f$ 0.41 (CHCl₃:MeOH:AcOH; 80-2-0.4). Anal. calc. for C₇₀H₁₂₇N₁₀O₂₃.H₂O (1494.87): C, 56.24; H, 8.69; N, 9.37. Found: C, 56.33; H, 8.32; N, 9.24.

EXAMPLE 19

H-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH

(N$^\alpha$-Desacetylthymosin α₁)

A solution of H-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu (134 mg, 0.0445 mmol) in TFE (4 mL) and Boc-Ser(tBu)-Asp(OtBu)-Ala-Ala-Val-Asp(OtBu)-Thr(tBu)-Ser(tBu)-Ser(tBu)-Glu(OtBu)-OH (164 mg, 0.111 mmol, 2.5 eq) was treated with HOBt (68 mg, 0.445 mmol, 10 eq) and cooled to 0°. DCC (50.5 mg, 0.245 mmol), 5.5 eq) was added to the cold stirring solution followed by the addition of N-methylmorpholine (to maintain pH ~8). Stirring proceeded for 1 hr at 0° and 23 h at 25°. The reaction mixture was poured into H₂O (50 mL) and the product was filtered, washed with ₂O (3×20 mL), MeOH (3×20 mL), DMSO (2×20 mL) and MeOH (3×20 mL) and dried in vacuo. Yield: 237 mg. The crude fully protected 28-peptide was deprotected with TFA:CH₂Cl₂ (5 mL: 5 mL) under N₂ at 25° for 2.5 h. The reaction mixture was poured into ether (200 mL) and the resultant precipitate washed with ether (2×25 mL) and dried in vacuo to give 185 mg of crude N$^\alpha$-desacetylthymosin α₁.

The crude product was taken up in H₂O, the pH adjusted to 8.0 (conc. NH₄OH) and loaded onto an ES Industries C$_\alpha$ 1.5×30 cm column [previously equilibrated with Pyr (3%):AcOH (3%)]. The column was eluted with Pyr (3%) AcOH (3%) for 60 min which was followed by gradient elution with 0°-13% CH₃CN for 60 min and finally held at Pyr (3%):AcOH (3%):CH₃CN (13%). Fractions (6 mL each) were collected at 2 min intervals and aliquots (20 μL) were analyzed by analytical HPLC using a gradient system. Fractions 79-83 were pooled and lyophilized to give pure N$^\alpha$-desacetylthymosin α₁ which was shown to have one major peak by HPLC that was identical to, and purer than, a reference standard.

EXAMPLE 20

N-Benzyloxycarbonyl-γ-t-butyl-L-glutamyl-L-asparagine t-butyl ester

A solution of Z-Glu(OtBu)-OH (212.5 g, 0.63 mol, 1.05 eq.) in DMF (400 mL) was placed in a 2-l 3-neck creased round bottom flask fitted with a thermometer, mechanical stirrer, dropping funnel and immersed in a dry ice-acetone bath at −15°. The reaction was carried out under an atmosphere of N₂, cooled to −15° and precooled (−20°) N-methylmorpholine (95.6 g, 0.945 mol, 1.575 eq.) added. After stirring for 4 min at −15°, the reaction mixture was cooled to −25° and precooled (−20°) isobutylchloroformate (86.0 g, 0.63 mol, 1.05 eq.) added portionwise over a 2 minute period (temperature must not exceed −15°). The reaction mixture stirred for an additional 4 min at −25° and a precooled (−20°) solution of H-Asn-OtBu (112.9 g, 0.60 mol, 1 eq.) in DMF (440 mL)-CH₂Cl₂ (40 mL) added as rapidly as possible while the temperature was maintained at −15° to −20°. After the addition was complete the reaction mixture was stirred at −15° for 30 min and at 25° for 2.5 h. The reaction mixture was filtered and the filter cake washed with DMF (2×50 mL). The filtrate was evaporated in vacuo and the resultant syrup dissolved in $CH_2Cl_2$ (2.5 l) and washed with 10% $NaHCO_3$ (2×450 mL), sat'd. NaCl (1×400 mL), 10% citric acid (3×450 mL), sat'd. NaCl (1×400 mL). It was dried ($MgSO_4$), filtered (celite) and evaporated to dryness to give a syrup which solidified on standing mp 136°–140°. Crystallization from isopropanol (1.1 l): ligroin (3 l) gave 269.9 g (88.6%) of white crystals; mp 143°–145°; $[\alpha]_D^{25} -19.06°$ (c 1, MeOH); $R_f$ 0.20 ($CHCl_3$:MeOH:AcOH; 80-2-0.4); $R_f$ 0.80 ($CHCl_3$:MeOH:AcOH; 80-10-0.4).

Anal. Calc. for $C_{25}H_{37}N_3O_8$(507.6): C, 59.16; H, 7.35; N, 8.28. Found: C, 59.24; H, 7.34; N, 8.40.

EXAMPLE 21

γ-t-Butyl-L-glutamyl-L-asparagine t-butyl ester

A solution of Z-Glu(OtBu)-Asn-OtBu (40.0 g, 0.079 mol) in MeOH (250 mL) containing 10% Pd-C (5.0 g) was reduced in a Parr hydrogenator[a] until the theoretical amount of $H_2$ was taken up (and no further uptake of $H_2$ was observed). The reaction mixture was filtered through celite (topped with a bed of $MgSO_4$) and evaporated to dryness. A total of 590 g of Z-Glu(OtBu)-Asn-OtBu was reduced and the combined material crystallized by treatment of the residue with MeOH. Evaporation of solvent resulted in the isolation of 397 g (91.4%) of white needles; mp 117°–119°; $[\alpha]_D^{25} -4.98°$ (c 1, MeOH); $R_f$ 0.25 ($CHCl_3$:MeOH:AcOH; 85-10-5). Anal. Calc. for $C_{17}H_{31}N_3O_6$ (373.5): C, 54.68; H, 8.37; N, 11.25. Found: C, 55.06; H, 8.76; N, 11.12.

[a] Alternatively, the Vibromixer apparatus may be used for larger scale hydrogenations.

EXAMPLE 22

N-Benzyloxycarbonyl-L-alanyl-γ-t-butyl-L-glutamyl-L-asparagine t-butyl ester

A solution of Z-Ala-OH (118.5 g, 0.53 mol, 1.05 eq.) in DMF (400 mL) was placed in a 2-l 3-neck creased round bottom flask fitted with a thermometer, mechanical stirrer, dropping funnel and immersed in a dry ice-acetone bath at −15°. The reaction was carried out under an atmosphere of $N_2$, cooled to −15° and precooled (−20°) N-methylmorpholine (80.9 g, 0.80 mol, 1.58 eq.) added. After stirring for 4 min at −15°, the reaction mixture was cooled to −25° and precooled (−20°) isobutylchloroformate (72.5 g, 0.53 mol, 1.05 eq.) added portionwise over a 2 min period (temperature must not exceed −15°). The reaction mixture stirred for an additional 4 min at −25° and a precooled (−20°) solution of H-Glu(OtBu)-Asn-OtBu (189 g, 0.506 mol) in DMF (350 mL)-$CH_2Cl_2$ (150 mL) added as rapidly as possible while maintaining −15° to −20° (4 minutes). After the addition was complete the reaction mixture was stirred at −15° for 30 min and at 25° for 3 h. The reaction mixture was filtered and the filter cake washed with DMF (2×50 mL). The filtrate was evaporated in vacuo and the resultant syrup immediately poured into $H_2O$ (3.5 l). The suspension was stirred for 18 h and the product collected by filtration and washed with $H_2O$ (2×500 mL) and dried in vacuo. A total of 575.6 g (93.9%) was prepared in 2 batches. Recrystallization from EtOH (3.5 l):$H_2O$ (5 l) gave 533.4 g (91.1%); mp 174°–176°; $[\alpha]_D^{25} -35.48°$ (c 1, MeOH); $R_f$ 0.25 ($CHCl_3$:MeOH:AcOH; 80-20-5).

Anal. Calc. for $C_{28}H_{42}N_4O_9$ (578.66): C, 58.12; H, 7.32; N, 9.68. Found: C, 57.81; H, 7.37; N, 9.44.

EXAMPLE 23

L-Alanyl-γ-t-butyl-L-glutamyl-L-asparagine t-butyl ester

A solution of Z-Ala-Glu(OtBu)-Asn-OtBu (40.0 g, 0.069 mol) in MeOH (200 mL) containing 10% Pd-C (5.0 g) was hydrogenated in a Parr hydrogenator[a] until the theoretical amount of $H_2$ was taken up (and no further uptake of $H_2$ was observed). The reaction mixture was filtered through celite (topped with a bed of $MgSO_4$) and evaporated to dryness. A total of 570.9 g of Z-Ala-Glu(OtBu)-Asn-OtBu was reduced and the combined material triturated with ether. The resultant while solid was filtered and dried in vacuo to give 427.6 g (97.5%); mp 112°–118°; $[\alpha]_D^{25} -18.96°$ (c 1, MeOH); $R_f$ 0.15 ($CHCl_3$:MeOH:AcOH; 80-20-5).

[a] Alternatively, the Vibromixer apparatus may be used for larger scale hydrogenations.

Anal. Calc. for $C_{20}H_{36}N_4O_7$ (444.53): C, 54.04; H, 8.16; N, 12.60. Found: C, 54.27; H, 7.98; N, 12.52.

EXAMPLE 24

N-Benzyloxycarbonyl-γ-t-butyl-L-glutamyl-L-alanyl-γ-t-butyl-L-glutamyl-L-asparagine t-butyl ester A solution of Z-Glu(OtBu)-OH (269.9 g, 0.80 mol, 1.04 eq.) in DMF (500 mL) was placed in a 3-l 3-neck creased round bottom flask fitted with a thermometer, mechanical stirrer, dropping funnel and immersed in a dry ice-acetone bath at −15°. The reaction was carried out under an atmosphere of $N_2$, cooled to −15° and precooled (−20°) N-methylmorpholine (125 g, 1.24 mol, 1.6 eq.) added. After stirring for 4 min at −15°, the reaction mixture was cooled to −35° and precooled (−20°) isobutylchloroformate (109.3 g, 0.80 mol, 1.04 eq.) added portionwise over a 3 min period (temperature must not exceed −15°). The reaction mixture stirred for an additional 4 min at −15°, cooled to −35° and a precooled (−20°) solution of H-Ala-Glu(OtBu)-Asn-OtBu (341.4 g, 0.768 mol, 1 eq) in DMF (750 mL) added as rapidly as possible while maintaining −15° to −20°. After the addition was complete the reaction mixture was stirred at −15° for 30 min and at 25° for 2½ h. The reaction mixture was slowly poured into $H_2O$ (9.5 l) while stirring rapidly and stirred for 2 h. The product was collected by filtration and washed with $H_2O$ (until the filtrate was free of $Cl^-$) and dried in vacuo. A total of 558.7 g was obtained. Recrystallization from $CH_3CN$ (refluxing required) gave 525.5 g (89.6%) of white solid; mp 212°–214°; $[\alpha]_D^{25} -15.82°$ (c 1, DMF); $R_f$ 0.83 ($CHCl_3$:MeOH:AcOH; 85-10-5).

Anal. Calc. for $C_{37}H_{57}N_5O_{12}$ (763.89): C, 58.18, H, 7.52; N, 9.17. Found: C, 58.48; H, 7.56; N, 9.37.

EXAMPLE 25

γ-t-Butyl-L-glutamyl-L-alanyl-γ-t-butyl-L-glutamyl-L-asparagine-t-butyl ester I

A suspension of Z-Glu(OtBu)-Ala-Glu(OtBu)-Asn-OtBu (147.3 g, 0.193 mol) in MeOH (1.6 L) containing 5% $Pd-BaSO_4$ (34.1 g) was hydrogenated in the Vibromixer apparatus for 3 h. The reaction mixture was filtered through celite and evaporated to 150 mL. Ether (1.4 L) was added and the resultant white solid was filtered and dried in vacuo. Yield: 103.1 g; second crop, 15.0 g (97.2%); mp 161°–164°; $[\alpha]_D^{25} -29.55°$ (c 1, MeOH); $R_f$ 0.70 (n-BuOH:AcOH:EtOAc:$H_2O$; 1-1-1-1); $R_f$ 0.26 ($CHCl_3$:MeOH:AcOH; 80-20-5).

Anal. Calc. for $C_{29}H_{51}N_5O_{10}$ (629.75): C, 55.31, H, 8.16; N, 11.12. Found: C, 55.05; H, 7.80; N, 11.29.

EXAMPLE 26

N-Benzyloxycarbonyl-L-valyl-γ-t-butyl-L-glutamic acid methyl ester

N-Benzyloxycarbonyl-L-valine (144 g, 0.58 mol, 1.2 eq) was dissolved in 400 ml freshly distilled THF and stirred mechanically in a 3-l 3-neck round bottom flask fitted with a thermometer and dropping funnel and immersed in a dry ice-alcohol bath at −15°. While stirring at −15°, N-methylmorpholine (55 ml, 0.58 mol, 1.2 eq) was added dropwise. The temperature was maintained at −15° and isobutylchloroformate (66.2 ml, 0.58 mol, 1.2 eq) was added dropwise over a 2 min period. The reaction mixture stirred for an additional 2 min at −15° and a precooled (−20°) solution of L-glutamic acid α-methyl ester γ-t-butyl ester.HCL (120.8 g, 0.48 mol) dissolved in 300 ml THF and 150 ml DMF was added dropwise with simultaneous addition of N-methylmorpholine (46 ml, 0.48 mol). [The addition took 6 min while maintaining the temperature below −15°.] The reaction mixture was stirred for 30 min at −15°, and for 3 h at 25°, evaporated in vacuo and the residue dissolved in EtOAc (900 ml) and washed with 10% $NaHCO_3$ (3×200 ml), 1M citric acid (3×200 ml) and satd. NaCl solution (1×200 ml). The aqueous washes were backwashed with EtOAc and the combined organic layers were dried over $MgSO_4$, filtered and concentrated to ~200 ml and pet. ether (1 l) added. The solid was collected and dried in vacuo[a] and the combined crops were recrystallized from $CCl_4$ (400 ml) pet. ether (1.2 l) to yield 168.5 g (78%) of white crystalline product;

[a]A second crop was obtained from the mother liquor.

mp 66.5°–68°; $R_f$ .74 (n-BuOH:AcOH:EtOAc:$H_2O$; 1-1-1-1), $R_f$ 0.73 ($CHCl_3$:$CH_3OH$:AcOH; 80-5-1); $[\alpha]_D^{25} -28.91°$, (c 1, MeOH). Anal. calc. for $C_{23}H_{24}N_2O_7$ (450.5): C, 61.32; H, 7.61; N, 6.22. Found: C, 61.23; H, 7.58; N, 6.01.

EXAMPLE 27

N-Benzyloxycarbonyl-L-valyl-L-valyl-γ-tert.butyl-L-glutamic acid α-methyl ester

N-Benzyloxycarbonyl-L-valyl-γ-tert.butyl-L-glutamic acid methyl ester (58.0 g, 128.8 mmol) was dissolved in DMF:THF (50 ml:160 ml), 5% Pd-$BaSO_4$ (12.8 g) added and hydrogenated in the Vibromixer apparatus for 2.5 h. The reaction mixture was filtered through celite, cooled to 0° and the resultant solution of L-valyl-γ-tert.butyl-L-glutamic acid methyl ester was placed in the freezer until used in the coupling stage below.[b]

[b]The intermediate must be coupled within several hours since it may undergo cyclization to the diketopiperazine. Retention of this intermediate at −30° will slow down this side reaction.

· N-Benzyloxycarbonyl-L-valine (38.8 g, 154.6 mmol, 1.2 eq) was dissolved in 45 ml freshly distilled THF in a 2-l 3-neck round bottom flask fitted with a thermometer, mechanical stirrer and dropping funnel and immersed in a dry ice-alcohol bath at −15°. While stirring at −15°, N-methylmorpholine (17.3 ml, 154.6 mmol) was added. This was followed by the addition of isobutylchloroformate (20.3 ml, 154.6 mmol) dropwise over a 2 min period. The reaction was stirred an additional 2 min at −15° and the precooled (−20°) solution of L-valyl-γ-tert.butyl-L-glutamic acid α-methyl ester (128.8 mmol from above) was added over a 2.7 min period. The reaction mixture was stirred at −15° for 30 min and at 25° for 17 h, evaporated in vacuo and the residue dissolved in $CHCl_3$ (600 ml) and washed with 10% $NaHCO_3$ (3×300 ml), satd. NaCl (1×300 ml), 1M citric acid (2×300 ml) and satd. NaCl (1×300 ml). The aqueous phases were backwashed with $CHCl_3$ and the combined organic layers dried over $MgSO_4$, filtered and evaporated in vacuo. The product was recrystallized from i-PrOH (4 l) to yield 41.6 g (59%) of white crystalline product; mp 203°–204°; $R_f$ 0.47 ($CHCl_3$:$CH_3OH$:AcOH; 80-2-0.4); $R_f$ 0.74 ($CHCl_3$:$CH_3OH$:AcOH; 80-5-1); $[\alpha]_D^{25} -7.40°$ (c 1, DMF). Anal. calc. for $C_{28}H_{43}N_3O_8$ (549.7): C, 61.18; H, 7.89, N, 7.64. Found: C, 61.43; H, 7.96; N, 7.41.

EXAMPLE 28

L-Valyl-L-valyl-γ-tert.butyl-L-glutamic acid α-methyl ester

N-Benzyloxycarbonyl-L-valyl-L-valyl-γ-tert.butyl-L-glutamic acid α-methyl ester (19.5 g, 35.5 mmol) was dissolved in 250 ml DMF, 5% Pd/$BaSO_4$ (6 g) added and hydrogenated in the Vibromixer apparatus for 3 h. The reaction mixture was filtered through celite, washed with ~50 ml DMF, and evaporated in vacuo to yield 14.7 g (100%) of white solid; mp 126°–127°; $R_f$ 0.35 ($CHCl_3$:$CH_3OH$:AcOH; 80:10:5); $[\alpha]_D^{25} -41.05°$ (c 1, $CH_3OH$). Anal. calc. for $C_{20}H_{37}N_3O_6$ (415.5): C, 57.81; H, 8.98; N, 10.11. Found: C, 57.45; H, 8.96; N, 9.99.

EXAMPLE 29

N-Benzyloxycarbonyl-γ-t-butyl-L-glutamyl-L-valyl-L-valyl-γ-t-butyl-L-glutamic acid α-methyl ester Z-Glu(OtBu)-OH (14.4 g, 42.6 mmol, 1.2 eq) was dissolved in THF (120 ml) and placed in a 1-l, 3-neck round bottom flask fitted with a thermometer, mechanical stirrer and immersed in a dry ice-alcohol bath at −15°. N-Methylmorpholine (4.5 ml, 42.6 mmol, 1.2 eq) was added while stirring at −15° and the isobutylchloroformate (5.4 ml, 42.6 mmol, 1.2 eq) added dropwise over a 2 min period. The reaction mixture was stirred for 2 min at −15° and a precooled (0°) solution of H-Val-Val-Glu(OtBu)-OMe (Ro 22-6610) (14.7 g, 35.5 mmol) in THF:DMF (100 ml:20 ml) added dropwise over a 3 min period maintaining the temperature at −15°. Stirring proceeded at −15° for 30 min and at 25° for 18 h. The reaction mixture was evaporated to dryness, the white solid triturated with i-PrOH and filtered. A second crop of product was obtained from the mother liquor. The total amount of product was 23 g (88%); mp 210°–211°, $R_f$ 0.58 ($CHCl_3$:$CH_3OH$:AcOH; 80-2-0.4); $[\alpha]_D^{25} -22.53°$ (c 1, DMSO). Anal. calc. for $C_{37}H_{58}N_4O_{11}$ (734.9); C, 60.47; H, 7.96; N, 7.62. Found: C, 60.44; H, 7.95; N, 7.61.

EXAMPLE 30

N-Benzyloxycarbonyl-Nε-tert-butyloxycarbonyl-L-lysine N-hydroxy-succinimide ester Z-Lys(Boc)-OH.DCHA (454 g; 0.808 mol) was stirred magnetically in ethyl acetate:0.5N $H_2SO_4$ (1.5 l:2 l) until all the white solid was in solution. The organic layer was collected, dried over $MgSO_4$, filtered and evaporated. The resultant free acid was placed in a 3-l, 3-neck round bottom flask fitted with a thermometer, drying tube and mechanical stirrer and stirred at 0° in ethyl acetate:dioxane (400 mL:1000 mL). N-Hydroxysuccinimide (93.0 g; 0.808 mol) and DCC (166.6 g;

0.808 mol) were added and the reaction stirred at 0° for 1 h and 25° for 16 h. The reaction mixture was filtered and the filtrate evaporated in vacuo. The oily residue was dissolved in i-PrOH (500 mL) and petroleum ether (~700 mL) added, cooled to 4° for several hours, then filtered to yield 350.4 g (91%) product: mp 95°–97°; $R_f$ 0.81 (CHCl$_3$:CH$_3$OH:AcOH; 80:5:1); $[\alpha]_D^{25}$ −17.76° (c 2, Dioxane).

EXAMPLE 31

N$^\alpha$-Benzyloxycarbonyl-N$^\epsilon$-t-butyloxycarbonyl-L-lysyl-N$^\epsilon$-t-butyloxycarbonyl-L-lysine A solution of Z-Lys(Boc)-OSu (239 g; 0.5 mol) in DMF (1.5 l) was stirred at 0° in a 3-l, 3-neck round bottom flask fitted with a mechanical stirrer and thermometer. The H-Lys(Boc)-OH (123 g; 0.5 mol) was added followed by Et$_3$N (70 mL; 0.5 mol). The reaction mixture was stirred at 0° for 30 min and at 25° for 18 h and evaporated in vacuo. The residue dissolved in EtOAc (1.5 l) and was washed with 1M citric acid (2×500 mL) and sat. NaCl solution (500 mL), dried over MgSO$_4$, filtered and dicyclohexylamine (100 mL) added. After standing in the cold room for several hours, the white salt was collected and dried to yield 379.8 g (96.4%); mp 114°–118°.

The free acid was generated from the DCHA salt as follows: Z-Lys(Boc)-Lys(Boc)-OH.DCHA (200 g; 0.25 mol) was stirred in ether; 0.5N H$_2$SO$_4$ (800 mL each) until all the solid was dissolved. The ether phase was extracted, dried over MgSO$_4$, filtered and evaporated in vacuo to an oil which was used directly in the next step. $[\alpha]_D^{25}$ −3.06° (c 1, MeOH); $R_f$ 0.52 (CHCl$_3$:MeOH:AcOH; 80:5:1).

Anal. Calc. for C$_{30}$H$_{48}$N$_4$O$_9$ (608.75); C, 59.19; H, 7.95; N, 9.20. Found: C, 58.76; H, 7.95; N, 9.15.

EXAMPLE 32

N$^\epsilon$-t-Butyloxycarbonyl-L-lysyl-N$^\epsilon$-t-butyloxycarbonyl-L-lysine The oily product from the preceding step (0.25 mol) was dissolved in CH$_3$OH (1.2 l) and hydrogenated with 5% Pd-BaSO$_4$ (30 g) for 4 h in a Vibromixer apparatus. The reaction mixture was filtered through celite and evaporated to dryness to yield 102.5 g (86.4%) of white solid; mp 189°–190°; $[\alpha]_D^{25}$ +18.19° (c 1, CH$_3$OH); $R_f$ 0.73 (n-BuOH:AcOH:EtOAc:H$_2$O; 1:1:1:1).

Anal. Calc. for C$_{22}$H$_{42}$N$_4$O$_7$ (474.60): C, 55.68; H, 8.92; N, 11.81. Found: C, 55.59; N, 8.73; N, 11.83.

EXAMPLE 33

N-Benzyloxycarbonyl-γ-t-butyl-L-glutamic acid N-hydroxysuccinimide ester

Z-Glu(OtBu)-OH (168.5 g; 0.5 mol) was dissolved in freshly distilled THF (1 l) and stirred at 0° in a 2-l, 3-neck round bottom flask fitted with a drying tube, mechanical stirrer and thermometer. While stirring at 0°, HOSu (63.6 g; 0.55 mol) and DCC (114 g; 0.55 mol) were added. The reaction mixture was stirred for 1 h at 0° and 18 h at 25°. At the end of this time the reaction mixture was filtered and the filtrate evaporated to dryness. The white solid was recrystallized from i-PrOH to yield 195.9 g (90.3%); mp 105°–106°; $R_f$ 0.66 (CHCl$_3$:CH$_3$OH:AcOH; 80:5:1); $[\alpha]_D^{25}$ −31.8° (c 1.8, EtOH)

EXAMPLE 34

N-Benzyloxycarbonyl-γ-t-butyl-L-glutamyl-N$^\epsilon$-t-butyloxycarbonyl-L-lysyl-N$^\epsilon$-t-butyloxycarbonyl-L-lysine, III A solution of Z-Glu(OtBu)-OSu (95.5 g; 0.22 mol; 1.1 eq.) in DMF (400 mL) was stirred at 0° in a 2-l, 3-neck round bottom flask fitted with a mechanical stirrer, thermometer and drying tube. H-Lys(Boc)-Lys(Boc)-OH (96.5 g; 0.2 mol) was added as a solid, portionwise, along with Et$_3$N (30.7 mL; 0.2 mol) and the pH of the reaction mixture adjusted to 8 with excess Et$_3$N [DMF (200 mL) was used to wash in all of the H-Lys(Boc)-Lys(Boc)-OH]. The reaction mixture was stirred at 0° for 1 h and at 25° for 18 h, then evaporated in vacuo. The residue was taken up in EtOAc (900 mL) and washed with 1M citric acid (2×400 mL) and sat. NaCl (600 mL), dried over MgSO$_4$, filtered and evaporated to ~½ volume. Ether (500 mL) was added and after cooling a white solid was collected to give 139.8 g (88%); mp 150°–152°; $R_f$ 0.83 (CHCl$_3$:CH$_3$OH:AcOH; 80:10:5); $R_f$ 0.49 (CHCl$_3$:CH$_3$OH:AcOH; 80:5:1); $[\alpha]_D^{25}$ −13.06 (c 1, CH$_3$OH).

Anal. Calc. for C$_{39}$H$_{63}$N$_5$O$_{12}$ (793.96): C, 59.00; H, 8.00; N, 8.82. Found: C, 58.77; H, 7.85; N, 8.93.

EXAMPLE 35

N-Benzyloxycarbonyl-L-leucine N-hydroxysuccinimide ester

Z-Leu-OH-DCHA (178.65 g; 0.4 mol) was stirred magnetically in ethyl acetate:0.5N H$_2$SO$_4$ (1 L:1 L) until all the white solid was in solution. The organic layer was collected, washed with 0.5N H$_2$SO$_4$ (3×300 mL) and distilled water (3×300 mL). The aqueous layers were combined and extracted with ethyl acetate. The organic layers were combined, dried (MgSO$_4$), filtered and evaporated. The resultant free acid (106.1 g; 0.4 mol) was dissolved in CH$_2$Cl$_2$ (300 mL) and placed in a 2 L, 3-necked round bottom flask fitted with a thermometer, drying tube and mechanical stirrer. N-Hydroxysuccinimide (50.63 g; 0.44 mol) and THF (100 mL) were added and the mixture stirred. The resultant solution was cooled (ice-bath), DCC (90.78 g; 0.44 mol) added and stirred at 0° for 1 h and 25° for 3.5 h. The reaction mixture was filtered and the filtrate evaporated in vacuo. The residue was dissolved in CH$_2$Cl$_2$ (450 mL), filtered (celite) hexane added to turbidity (1.1 L) and stored at 4° for 12 h. The crystals were filtered and dried yielding 122.8 g (84.7%) of product: m.p. 115°–117°; $[\alpha]_D^{25}$ −32.35° (c 1, dioxane).

EXAMPLE 36

N-Benzyloxycarbonyl-L-leucyl-N$^\epsilon$-t-butyloxycarbonyl-L-lysine

A solution of Z-Leu-OSu (122.5 g, 0.338 mol) in DMF (1.2 L) was stirred at 0° in a 3 L, 3-necked round bottom flask fitted with a mechanical stirrer and thermometer. The H-Lys(Boc)-OH (83.26 g, 0.338 mol) was added and the solution stirred at 0° for 15 min. Triethylamine (47.6 mL, 0.338 mol) was added and the reaction mixture stirred at 0° for 30 min and 25° for 3 h. Additional triethylamine (20 mL) was added to maintain the pH at 8 and the reaction mixture stirred for an additional 20 h. At the end of this time, tlc showed some unreacted H-Lys(Boc)-OH and the reaction mixture was stirred for an additional 24 h (pH 8). The reaction mixture was cooled (0°), acidified with glacial acetic acid (160 mL) and evaporated in vacuo. The residue (oil) was dissolved in EtOAc (1.5 L) and washed with 1M citric acid (2×600 mL) and 10% NaCl (2×700 mL), dried (MgSO₄), filtered and concentrated in vacuo. The oily residue was dissolved in anhydrous ether (4 L) and dicyclohexylamine (70.7 mL) added followed by the addition of 1 L of ether. After standing in the cold room for 72 h, the white salt was collected and dried to yield 210.8 g (90%); m.p. 125°–128° (recrystallization of an analytical sample increased the m.p. to 143°–146°); $[\alpha]_D^{25} -4.17$ (c 1, MeOH); $R_f$ 0.39 (CHCl₃:MeOH:AcOH; 85:10:5). The free acid was generated from the DCHA salt in the following manner: Z-Leu-Lys(Boc)-OH·DCHA (201.9 g, 0.291 mol) was stirred in EtOAC:0.5N H₂SO₄ (2 L:727 mL) until all the solid dissolved. The organic layer was separated, washed with 0.5N H₂SO₄ (730 mL), dried (MgSO₄) and evaporated in vacuo. Yield: 150.6 g (100%) $[\alpha]_D^{25} +3.38°$ (c 1, CHCl₃); tlc $R_f$ 0.64 (CHCl₃:MeOH:AcOH; 85:10:5).

Anal. Calc. for C₂₅H₃₉N₃O₇ (493.6): C, 60.83; H, 7.96; N, 8.51. Found: C, 60.37; H, 8,08; N, 8.44.

EXAMPLE 37

L-Leucyl-N$^\epsilon$-tert-butyloxycarbonyl-L-lysine

A solution of Z-Leu-Lys(Boc)-OH 41.5 g, 0.084 mol) in methanol (210 mL) was hydrogenated in a Vibromixer apparatus using 10% Pd/C (5.0 g) for 3.5 h. The precipitated product dissolved on addition of H₂O (120 mL). The catalyst was removed by filtration (celite); washed twice with H₂O and the combined filtrate evaporated to near dryness. The residue was reevaporated from MeOH (2×) and Et₂O (2×). The solid product was collected, washed with Et₂O and dried to afford 26.9 g of white solid. Recrystallization from warm iPrOH (420 mL) and MeOH (350 mL) afforded, after drying, 24.6 g of white crystalline product (81.5%); mp 142°–143°; $R_f$ 0.63 (n-BuOH:AcOH:EtOAc:H₂O; 1-1-1-1); $[\alpha]_D^{25} +20.76°$ (c 1, MeOH). Anal. calcd. for C₁₇H₃₃N₃O₅ (359.47): C, 56.80; H, 9.25; N, 11.69. Found: C, 56.72; H, 9.55; N, 11.57.

EXAMPLE 38

N-Benzyloxycarbonyl-β-tert-butyl-L-aspartic acid N-hydroxysuccinimide ester

Z-Asp(OtBu)-OH·DCHA (378 g; 0.750 mol) was stirred magnetically at 0° in a mixture of ethyl acetate:0.5N H₂SO₄ (3.0 L:1.875 L) until all the white solid was in solution. The organic layer was collected, washed with ice-cold 0.5N H₂SO₄ (1.8 L), water (3×1 L), dried (MgSO₄), filtered and evaporated in vacuo. Yield: 252 g (100%); $R_f$ 0.63 (CHCl₃:MeOH:AcOH; 85:10:5); $[\alpha]_D^{25} -10.10°$ (c 1, pyridine). The resultant free acid (252 g; 0.75 mol) and N-hydroxysuccinimide (94.95 g; 0.825 mol) were placed in a 12 L, 3-necked round bottom flask fitted with a thermometer, drying tube, mechanical stirrer and stirred at 25° in THF (4.2 L). After all the solids had dissolved, the reaction mixture was cooled (0°), DCC (170.2 g; 0.825 mol) and THF (0.75 L) added and stirred at 0° for 1 h and 25° for 5 h. The reaction mixture was filtered and the filtrate evaporated in vacuo. The residue was dissolved in CH₂Cl₂ (2 L) and stored (0°). The solution was filtered (to remove some more DCU) and the filtrate evaporated in vacuo. The residue was dissolved in CH₂Cl₂ (warm):hexane (1 L:4 L) and stored (0°). The resultant crystals were washed with hexane:CH₂Cl₂ (9:1) (1 L), hexane (1 L) and dried. Yield: 274 g (86.5%); m.p. 150°–151°; $[\alpha]_D^{25} -26.36°$ (c 1, DMF).

EXAMPLE 39

N-Benzyloxycarbonyl-β-tert-butyl-L-aspartyl-L-leucyl-N$^\epsilon$-tert-butyloxycarbonyl-L-lysine, IV A solution of Z-Asp(OtBu)-OSu (115.6 g; 0.275 mol) in DMF (1.16 L) was stirred at 0° in a 3 L, 3-necked round bottom flask fitted with a mechanical stirrer and thermometer. The H-Leu-Lys(Boc)-OH (89.86 g; 0.250 mol) was added followed by Et₃N (35.2 mL; 0.25 mol). The reaction mixture was stirred at 0° for 0.5 h and at 25° for 1.5 h. Additional Et₃N (17 mL) was added (to maintain pH 8) and the reaction mixture stirred at 25° for 20 H. The reaction mixture was evaporated, dissolved in EtOAc (3 L), washed with 1M citric acid (3×1 L), H₂O (3×1 L), dried (MgSO₄) and evaporated in vacuo. The residual paste was dissolved in anhydrous ether (5 L) and stirred magnetically while DCHA (53.5 mL; 0.268 mol) was added slowly. After standing in the cold room (20 h) the white salt was collected and washed with anhydrous ether (2×0.5 L) and petroleum ether (2×0.5 L). Yield: 177 g (84%); m.p. 173°–174°; $[\alpha]_D^{25} -12.57°$ (c 1, MeOH).

Z-Asp(OtBu)-Leu-Lys(Boc)-OH·DCHA (198 g; 0.234 mol) was stirred at 0° in a mixture of EtOAc:0.5N H₂SO₄ (3.2 L:1.19 L) until all the solid was dissolved. The organic layer was collected, washed with H₂O (4×1 L), dried (MgSO₄), filtered and evaporated in vacuo. The residue (froth) was triturated with pet. ether and dried. Yield: 165.5 g (100%); $[\alpha]_D^{25} -1.16°$ (c 1, CHCl₃); $R_f$ 0.73 (CHCl₃:MeOH:AcOH; 85:10:5). Lit.[2] $R_f$ 0.66; $[\alpha]_D^{25} -1.25$ (c 1, CHCl₂).

Anal. Calc. for C₃₃H₅₂N₄O₁₀ (664.8): C, 59.62; H, 7.88; N, 8.43. Found: C, 59.38; H, 8.13; N, 8.45.

EXAMPLE 40

N$^\epsilon$-t-Butyloxycarbonyl-L-lysine phenyl ester tosylate

Z-Lys(Boc)-OPh (143 g, 313 mmol) and Tos-OH·H₂O (59.54 g, 313 mmol) were dissolved in 1 l DMF and hydrogenated in the presence of 10% Pd-C. The solution was filtered and concentrated in vacuo to ~500 ml. Crystallization was achieved by the addition of ethyl acetate (5 l).

Yield: 136 g (87%); mp. 163°–165°; $[\alpha]_D^{20} +8.3°$ (c=1, DMF).

Anal. Calc. for C₂₄H₃₄N₂O₇S (494.6): C, 58.28; H, 6.93; N, 5.66; S, 6.48. Found: C, 58.05; H, 6.94; N, 5.54; S, 6.79.

EXAMPLE 41

N-Benzyloxycarbonyl-O-t-butyl-L-threonyl-N$^\epsilon$-t-butyloxycarbonyl-L-lysine phenyl ester Z-Thr(tBu)-OH (180.35 g, 583 mmol) was dissolved in 850 ml DMF and cooled to −35° C. While stirring at −35° C., N-methyl-morpholine (64.2 ml, 583 mmol) was added, followed by the addition of isobutyl chloroformate (76.2 ml, 583 mmol). The reaction mixture was activated for 2 min. at −15° C. and quickly cooled to −30° C. A precooled solution (−25° C.) of H-Lys(Boc)-OPh·Tos-OH (262.1 g, 530 mmol) in 800 ml DMF and N-methyl-morpholine (58.4 ml, 530 mmol) were added simultaneously. The reaction mixture was stirred for 15 min. at −15° C. and 1 h at 25° C. and evaporated in vacuo. The residue was dissolved in 3 l ethyl acetate and washed with 10% Na₂CO₃ sol. (3×1.5 l), satd.

NaCl sol. (4×1 l), 5% KHSO$_4$/10% K$_2$SO$_4$ sol. (3×1.5 l), and satd. NaCl-sol., dried over Na$_2$SO$_4$, filtered and evaporated in vacuo. The residue was crystallized from ether (1 l)/hexane (3 l) or from isopropyl acetate (1.5 l)/hexane (4 l).

Yield: 258.4 g (79.5%); mp. 72° C.*; $[\alpha]_D^{20}+11.8°$ (c=1, CHCl$_3$).

*When the material was crystallized from isopropyl acetate/hexane a melting point of 106° C. resulted.

Anal. Calc. for C$_{33}$H$_{47}$N$_3$O$_8$ (613.75): C, 64.58; H, 7.72; N, 6.85. Found: C, 64.42; H, 7.90; N, 6.57.

EXAMPLE 42

N-Benzyloxycarbonyl-O-t-butyl-L-threonyl-O-t-butyl-L-threonyl-N$^\epsilon$-t-butyloxycarbonyl-L-lysine phenyl ester Z-Thr(tBu)-Lys(Boc)-OPh (251.6 g, 410 mmol) dissolved in 1 l DMF was hydrogenated in the presence of Tos-OH.H$_2$O (78 g, 410 mmol) and 10% Pd-C. After the hydrogenation was completed the catalyst was filtered off.

Z-Thr(tBu)-OH (139.2 g, 450 mmol) was dissolved in 700 ml DMF and cooled to −35° C. While stirring at −35° C., N-methylmorpholine (49.6 ml, 450 mmol) was added, followed by the addition of isobutyl chloroformate (58.8 ml, 450 mmol). The reaction mixture was activated for 2 min. at −15° C. and quickly cooled to −30° C. The precooled (−25° C.) DMF solution from the hydrogenation step and N-methylmorpholine (45.2 ml, 410 mmol) were added simultaneously. The reaction mixture was stirred for 15 min. at −15° C. and 1 h at 25° C. and evaporated in vacuo. The residue was dissolved in 2 l ethyl acetate and washed with 10% Na$_2$CO$_3$ sol. (3×1.5 l); satd. NaCl-sol. (1×1 l), 5% KHSO$_4$/10% K$_2$SO$_4$ sol. (3×1.5 l), and satd. NaCl-sol., dried over Na$_2$SO$_4$, filtered and evaporated in vacuo. The residue was crystallized from ether (1 l)/hexane (4 l).

Yield: 240.2 g, 76%; mp. 124° C. $[\alpha]_D^{20}+26.4°$ (c=1, CHCl$_3$).

Anal. Calc for C$_{41}$H$_{62}$N$_4$O$_{10}$ (770.97): C, 63.87; H, 8.11; N, 7.27. Found: C, 63.81; H, 8.56; N, 7.06.

EXAMPLE 43

N-Benzyloxycarbonyl-L-isoleucyl-O-t-butyl-L-threonyl-O-t-butyl-L-threonyl-N$^\epsilon$-t-butyloxycarbonyl-L-lysine phenyl ester A solution of Z-Thr(tBu)-Thr(tBu)-Lys(Boc)-OPh (346.9 g, 450 mmol) in 1 l DMF was hydrogenated in the presence of Tos-OH.H$_2$O (85.6 g, 450 mmol) and 10% Pd-C. After the hydrogenation was completed the catalyst was filtered off.

Z-Ile-OH (132.66, 500 mmol) was dissolved in 700 ml DMF and cooled to −35° C. While stirring at −35° C., N-methylmorpholine (55 ml, 500 mmol) was added, followed by the addition of isobutyl chloroformate (65 ml, 500 mmol). The reaction mixture was activated for 5 min. at −15° C. and quickly cooled to −20° C. The precooled DMF solution (−25° C.) from the hydrogenation step and N-methylmorpholine (50 ml, 450 mmol) were added simultaneously. The reaction mixture was stirred for 15 min. at −15° C. and 1 h at 25° C. and evaporated in vacuo. The residue was dissolved in 3 l ethyl acetate and washed with 10% Na$_2$CO$_3$ sol. (2×1.5 l), satd. NaCl-sol. (1×1 l), 5% KHSO$_4$/10% K$_2$SO$_4$ sol. (2×1.5 l) and satd. NaCl-sol., dried over Na$_2$SO$_4$, filtered and evaporated in vacuo. The residue was crystallized from ethyl acetate (2 l)/ether (2 l).

Yield: 296 g (74.5%); mp. 150° C.; $[\alpha]_D^{20}+24.2°$ (c=1, CHCl$_3$) C$_{47}$H$_{73}$N$_5$O$_{11}$ (884.12).

Anal. Calc. for C$_{47}$H$_{73}$N$_5$O$_{11}$ (884.12): C, 63.85; H, 8.32; N, 7.92. Found: C, 63.77; H, 8.34; N, 7.92.

EXAMPLE 44

N-Benzyloxycarbonyl-L-isoleucyl-O-t-butyl-L-threonyl-O-t-butyl-L-threonyl-N$^\epsilon$-t-butyloxycarbonyl-L-lysine, V Z-Ile-Thr(tBu)-Thr(tBu)-Lys(Boc)-OPh (0.884 g, 1.0 mmol) was dissolved in 25 ml acetone and 4 ml H$_2$O added followed by the addition of 3% H$_2$O$_2$(1.16 ml, 1.0 mmol) and the solution stirred magnetically. The pH was adjusted to, and maintained at, 10.5 by the addition of 0.1N NaOH$^{(a)}$ after stirring at pH 10.5 for 1.5 h, 0.1N HCl was added until the reaction mixture reached pH 3. The white solid which formed was collected by filtration,$^{(b)}$ washed with H$_2$O (∼60 ml) and dried in vacuo to yield 0.781 g (96.6%); mp 174°–176° dec;$^{(c)}$ Rf 0.63 (ChCl$_3$:CH$_3$OH:AcOH; 80-5-1); $[\alpha]_D^{25}+13.66$ (c 1, CH$_3$OH). Anal: calc. for C$_{41}$H$_{69}$N$_5$O$_{11}$(808.0): C, 60.94; H, 8.61; N, 8.67. Found: C, 60.83; H, 8.70; N, 8.93.

$^{(a)}$An autotitrator is recommended for larger scale reactions.
$^{(b)}$ For larger scale reactions, the procedure may have to be repeated if there is still starting material present at this stage according to tlc.
$^{(c)}$ The product from another run gave material with mp 179°–180°.

EXAMPLE 45

N-Benzyloxycarbonyl-γ-t-butyl-L-glutamic acid phenyl ester

Z-Glu(OtBu)-OH (202.4 g, 0.6 mol) was dissolved in 1.5 l ethyl acetate and cooled to 0° C. To the stirred solution pyridine (48.4 ml, 0.6 mol), phenol (56.5 g, 0.6 mol) and a precooled solution of DCCI (123.8 g, 0.6 mol) in about 300 ml ethyl acetate were added. The reaction mixture was stirred for 2 h at 0° C. and for 20 h at room temperature. The reaction mixture was stirred for another 30 min. after the addition of acetic acid (2 ml). Dicyclohexylurea was filtered off and the filtrate was washed with 10% NaHCO$_3$-sol., satd. NaCl sol., 5% KHSO$_4$/10%K$_2$SO$_4$-sol., satd. NaCl sol. and dried over Na$_2$SO$_4$. The filtrate was concentrated and crystallized by adding petroleum ether.

Yield: 206 g (83%); mp. 74° C.; $[\alpha]_D-27°$ (c=1, DMF).

Anal.: Calc. for C$_{23}$H$_{27}$NO$_6$(413.47): C, 66.81; H, 6.58; N, 3.39. Found: C, 66.65; H, 6.71; N, 3.44.

EXAMPLE 46

N-Benzyloxycarbonyl-O-t-butyl-L-seryl-γ-t-butyl-L-glutamic acid phenyl ester

A solution of Z-Glu(OtBu)-OPh (198.4 g, 480 mmol) in 1 l DMF was hydrogenated in the presence of Tos-OH.H$_2$O (91.3 g, 480 mmol) and 10% Pd-C (20 g). After the hydrogenation was completed the catalyst was filtered off.

Z-Ser(tBu)-OH (147.7 g, 500 mmol) was dissolved in 1.5 l DMF and cooled to −25° C. N-Methylmorpholine (55.1 ml, 500 mmol) and isobutyl chloroformate (65.35 ml, 500 mmol) were added and 2 min. were allowed for activation at −15° C. The pre-cooled DMF solution (−25° C.) from the hydrogenation step and N-methylmorpholine (52.9 ml, 480 mmol) were added simultaneously. The reaction mixture was stirred for 15 min. at −15° C. and 1 h at 25° C. and evaporated in vacuo. The residue was dissolved in 4 l ethyl acetate extracted with 10% NaHCO$_3$-sol., 5% KHSO$_4$/10%K$_2$SO$_4$-sol. and satd. NaCl-sol., dried over Na$_2$SO$_4$, filtered and evaporated. The residue was crystallized from ether/hexane.

Yield: 223 g (83.5%); mp. 97° C.; $[\alpha]_D^{20}$ +16.2° (c=1, CHCl$_3$).

Anal. Calc. for C$_{30}$H$_{40}$N$_2$O$_8$ (556.66): C, 64.73; H, 7.24; N, 5.03. Found: C, 64.82; H, 7.22; N, 5.10.

EXAMPLE 47

N-Benzyloxycarbonyl-O-t-butyl-L-seryl-O-t-butyl-L-seryl-γ-t-butyl-L-glutamic acid phenyl ester A solution of Z-Ser(tBu)-Glu(OtBu)-OPh (256.1 g, 460 mmol) in 1.2 l DMF was hydrogenated in the presence of Tos-OH.H$_2$O (87.5 g, 460 mmol) and 10% Pd-C (~25 g). After the hydrogenation was completed the catalyst was filtered off.

Z-Ser(tBu)-OH (145.6 g, 493 mmol) was dissolved in 1.4 DMF and cooled to −25° C. N-Methylmorpholine (54.3 ml, 493 mmol) and isobutyl chloroformate (64.4 ml, 493 mmol) were added to this solution and 2 min. were allowed for activation at −15° C. The precooled DMF solution from the hydrogenation step and N-methylmorpholine (50.7 ml, 460 mmol) were added simultaneously. The reaction mixture was stirred for 15 min. at −15° C. and 1 h at 25° C. and evaporated in vacuo. The residue was dissolved in 4 l ethyl acetate and extracted with 10% NaHCO$_3$-sol., 5% KHSO$_4$/10% K$_2$SO$_4$-sol., and satd. NaCl-sol., dried over Na$_2$SO$_4$, filtered and evaporated. The residue was crystallized from ethyl acetate/hexane.

Yield: 262 g (81.4%); mp 130°-31° C.; $[\alpha]_D^{20}$ +21.6° (c=1, CHCl$_3$).

Anal. Calc. for C$_{37}$H$_{53}$N$_3$O$_{10}$ (699.84): C, 63.50; H, 7.63; N, 6.00. Found: C, 63.37; H, 7.95; N, 6.03.

From the motherliquor another crop of 26 g (8%) was obtained. Total yield: 288 g (89.5%).

EXAMPLE 48

N-Benzyloxycarbonyl-O-t-butyl-L-threonyl-O-t-butyl-L-seryl-O-t-butyl-L-seryl-γ-t-butyl-L-glutamic acid phenyl ester A solution of Z-Ser(tBu)-Ser(tBu)-Glu(OtBu)-OPh (270 g, 386 mmol) in 1.2 l DMF was hydrogenated in the presence of Tos-OH.H$_2$O (73.4 g, 386 mmol) and 10% Pd-C (30 g). After the hydrogenation was completed the catalyst was filtered off.

Z-Thr(tBu)-OH (119.4 g, 386 mmol) was dissolved in 1.2 l DMF and cooled to −25° C. N-Methylmorpholine (42.5 ml, 386 mmol) and isobutyl chloroformate (50.5 ml, 386 mmol) were added to this solution and 2 min. were allowed for activation at −15° C. The precooled DMF solution from the hydrogenation step and N-methylmorpholine (42.5 ml, 386 mmol) were added simultaneously. The reaction mixture was stirred for 15 min. at −15° C. and 1 h at 25° C. and evaporated in vacuo. The residue was dissolved in 4 l ethyl acetate, extracted with 10% NaHCO$_3$-sol., 5% KHSO$_4$/10% K$_2$SO$_4$-sol., and satd. NaCl-sol., dried over Na$_2$SO$_4$, filtered and evaporated. The residue was crystallized from ethyl acetate/hexane.

Yield: 270.5 g (81.8%); mp. 144°-45° C.; $[\alpha]_D^{20}$ +37.2° (c=1, CHCl$_3$).

Anal. Calc. for C$_{45}$H$_{68}$N$_4$O$_{12}$ (857.06): C, 63.05; H, 8.00; N, 6.54. Found: C, 62.71; H, 8.18; N, 6.57.

From the motherliquor another crop of 19.6 g (6%) was obtained. Total yield: 290.1 g (87.7%).

EXAMPLE 49

N-Benzyloxycarbonyl-L-valyl-β-t-butyl-L-aspartic acid

To a stirred suspension of H-Asp(OtBu)-Oh (18.9 g, 100 mmol) in 400 ml DMF at 0° C. triethylamine (13.9 ml, 100 mmol) was added followed by Z-Val-OSu (38.3 g, 110 mmol) and pyridine (8.1 ml, 100 mmol). The reaction mixture was stirred at 0° C. for 2 h and at 25° C. for 20 h. The clear reaction mixture was evaporated to dryness and the residue distributed between ethyl acetate and 5% KHSO$_4$/10% K$_2$SO$_4$ sol. The org. layer was washed with 5% KHSO$_4$/10% K$_2$SO$_4$ sol., satd. NaCl sol., dried over Na$_2$SO$_4$, filtered and evaporated in vacuo. The residue was crystallized and recrystallized from ethyl acetate/hexane.

Yield: 35.9 g (85%); mp. 138°-39° C.; $[\alpha]_D^{20}$ −9.7° (c=1, MeOH).

Anal. Calc. for C$_{21}$H$_{30}$N$_2$O$_7$ (422.48); C, 59.70; H, 7.16; N, 6.63. Found: C, 59.64; H, 7.15; N, 6.55.

EXAMPLE 50

N-Benzyloxycarbonyl-L-alanyl-L-valyl-β-t-butyl-L-aspartic acid

A solution of Z-Val-Asp(OtBu)-OH (31.7 g, 75 mmol) in 500 ml methanol/25 ml water was hydrogenated in the presence of 10% Pd-C. The hydrogenation mixture was heated, filtered and evaporated in vacuo. The crystalline residue was suspended in 300 ml DMF and cooled to 0° C. N-Methylmorpholine (8.25 ml, 75 mmol) was added followed by Z-Ala-OSu (24 g, 75 mmol) and pyridine (6.05 ml, 75 mmol). The reaction mixture was stirred at 0° C. for 4 h and at 25° C. for 18 h. The mixture was evaporated in vacuo and the residue was distributed between ethyl acetate and 5% KHSO$_4$/K$_2$SO$_4$-sol. Sufficient water-saturated n-butanol was added to dissolve the crystallizing compound in the organic phase. The organic phase was washed with water (5×200 ml) and evaporated in vacuo. The residue was crystallized from ethyl acetate/isopropyl acetate.

Yield: 30.5 g (82.5%); mp 168° C.; $[\alpha]_D^{20}$ −37.2° (c=1, MeOH).

Anal. Calc. for C$_{24}$H$_{35}$N$_3$O$_8$ (493.56): C, 58.41; H, 7.15; N, 8.51. Found: C, 58.47; H, 7.43; N, 8.44.

EXAMPLE 51

Z-Ala-Val-Asp(OtBu)-Thr(tBu)-Ser(tBu)-Ser(tBu)-Glu(OtBu)-OPh

A solution of Z-Thr(tBu)-Ser(tBu)-Ser(tBu)-Glu(OtBu)-OPh (200 g, 233 mmol) in 1.2 l DMF was hydrogenated in the presence of Tos-OH.H$_2$O (44.4 g, 233 mmol) and 10% Pd-C (20 g). After the hydrogenation was completed the catalyst was filtered off.

Z-Ala-Val-Asp(OtBu)-OH (123.4 g, 250 mmol) was dissolved in 1.5 l DMF and cooled to −25° C. N-Methylmorpholine (27.5 ml, 250 mmol) and isobutyl chloroformate (32.7 ml, 250 mmol) were added to this solution and 2 min. were allowed for activation at −15° C. The precooled DMF solution from the hydrogenation step and N-methylmorpholine (25.7 ml, 233 mmol) were added simultaneously. The reaction mixture was stirred for 15 min. at −15° C. and 1 h at 25° C. and poured into 15 l water which contained NaHCO$_3$ (23.5 g, 280 mmol). The resulting solid was collected, washed with water and dried in vacuo. This solid was dissolved under warming in chloroform and crystallized by the addition of hexane.

Yield: 260 g (93%); mp. 236°–237° C.; $[\alpha]_D^{20}+19.4°$ (c=1, CHCl$_3$).

Anal.: Calc. for C$_{61}$H$_{95}$N$_7$O$_{17}$ (1198.46): C, 61.13; H, 7.99; N, 8.18. Found: C, 60.92; H, 8.00; N, 8.17.

EXAMPLE 52

N-Benzyloxycarbonyl-β-t-butyl-L-aspartyl-L-alanine benzyl ester

Z-Asp(OtBu)-OH (161,6 g, 500 mmol) was dissolved in 750 ml DMF and cooled to −30° C. To the stirred solution N-methylmorpholine (55,1 ml, 500 mmol) and isobutyl chloroformate (65,4 ml, 500 mmol) were added and 2 min allowed for activation at −15° C. A pre-cooled DMF (500 ml) solution of H-Ala-OBzl×Tos-OH (193,3 g, 550 mmol) and N-methylmorpholine (60,6 ml, 550 mmol) were added simultaneously. The reaction mixture was stirred at −15° C. for 15 min and at 25° C. for 1 h. The reaction mixture was evaporated in vacuo and the residue was taken up in 3,5 l ethyl acetate. The organic layer was extracted with 10% Na$_2$CO$_3$-sol., water, 5% KHSO$_4$/10% K$_2$SO$_4$-sol. and saturated NaCl sol., dried over Na$_2$SO$_4$, filtered and evaporated in vacuo. Crystallisation was achieved at 0° C. from ethyl acetate (0,5 l)/hexane (5 l).

Yield: 202,9 g (83,8%); mp. 51° C.; $[\alpha]_D^{25}-26,9°$ (c=1, MeOH).

Anal.: Calc. for C$_{26}$H$_{32}$N$_2$O$_7$ (484.54): C, 64.45; H, 6.66; N, 5.78. Found: C, 64.45; H, 6.69; N, 5.75.

EXAMPLE 53

N-Benzyloxycarbonyl-O-t-butyl-L-seryl-β-t-butyl-L-aspartyl-L-alanine

A solution of Z-Ser(tBu)-OH (29,5 g, 100 mmol) in 300 ml ethyl acetate was cooled to 0°. N-Hydroxysuccinimide (11,5 g, 100 mmol) and DCC (22,7 g, 110 mmol) were added and the reaction stirred at 0° for 1 h and at 25° for 20 h. The unreacted DCC was destroyed by adding Tos-OH-H$_2$O (0,2 g) and water (5 ml). After 1 h stirring at 25° the urea was filtered off and the filtrate evaporated in vacuo.

Z-Asp(OtBu)-Ala-OBzl (43,6 g, 90 mmol) was dissolved 1 liter DMF and hydrogenated in the presence of Tos-OH.H$_2$O (17,1 g, 90 mmol) and 10% Pd-C. After the hydrogenation was completed the catalyst was filtered off. The filtrate was cooled to 0°, neutralized with N-methylmorpholine (9,9 ml, 90 mmol) and added to Z-Ser(tBu)-OSu. Another portion of N-methylmorpholine (9,9 ml, 90 mmol) was added and the reaction mixture was stirred at 0° for 1 h and at 25° for 18 h. 2-Diethylamino-ethylamine (2,83 ml, 20 mmol) was added to the reaction mixture and stirring was continued for 4 h. The solution was evaporated in vacuo, the residue dissolved in 0,5N NaOH (0,5 l) and extracted with ether (3×0,2 l). To the alkaline phase 0,4 l ethyl acetate was added and acidified with 5% KHSO$_4$/10% K$_2$SO$_4$-solution. The acidic layer was again extracted with ethyl acetate (2×0,3 l). The combined organic layers were washed with 5% KHSO$_4$/10% K$_2$SO$_4$-sol. (1×0,3 l) and saturated NaCl-sol., dried over Na$_2$SO$_4$, filtered and evaporated in vacuo.

Yield: 37 g (76,5%)Oil.

EXAMPLE 54

N-Acetyl-O-t-butyl-L-seryl-β-t-butyl-L-aspartyl-L-alanine

The oily product Z-Ser(tBu)-Asp(OtBu)-Ala-OH (16,3 g, 30 mmol) from the preceding step was dissolved in 200 ml methanol and hydrogenated with 10% Pd-C. The catalyst was filtered off and the filtrate evaporated to dryness. The residue was dissolved in 100 ml DMF, cooled to 0° and N-methylmorpholine (6,6 ml, 60 mmol) and acetic anhydride (4,25 ml, 45 mmol) were added under stirring. The reaction mixture was stirred for 15 min at 25° and evaporated in vacuo. The residue was dissolved in 1N NaOH and extracted with ethyl acetate. The alkaline phase was acidified with 5% KHSO$_4$/10% K$_2$SO$_4$-sol., saturated with K$_2$SO$_4$ and several times extracted with ethyl acetate. The combined organic layers were washed with saturated NaCl-sol., dried over Na$_2$SO$_4$ and evaporated to dryness. The residue was crystallized from isopropyl acetate/ether.

Yield: 8,4 g (62,7%); m.p. 112°; $[\alpha]_D^{25}-16,6°$ (c=5, MeOH).

Anal. Calc. for C$_{20}$H$_{35}$N$_3$O$_8$ (445.51): C, 53,92; H, 7,92; N, 9,43. Found: C, 54,03; H, 8,00; N, 9,34.

We claim:

1. A compound of the formula
Ac-Ser(tBu)-Asp(OtBu)-Ala-Ala-Val-Asp(OtBu)-Thr(tBu)-Ser(tBu)-Ser(tBu)-Glu(OtBu)-OH
wherein Ac is acetyl and tBu is tert.butyl.

2. A compound of the formula
H-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu)-Glu(OtBu)-Ala-Glu(OtBu)-Asn-OtBu
wherein tBu is tert.butyl and Boc is tert.butyloxycarbonyl.

3. A compound of the formula
Z-Ile-Thr(tBu)-Thr(tBu)-Lys(Boc)-Asp(OtBu)-Leu-Lys(Boc)-Glu(OtBu)-Lys(Boc)-Lys(Boc)-Glu(OtBu)-Val-Val-Glu(OtBu) Glu(OtBu)-Ala-Glu(OtBu)-Asn-OtBu wherein Z is benzyloxycarbonyl, Boc is tert.butyloxycarbonyl and tBu is tert.-butyl.

4. A compound of the formula
Ac-Ser(tBu)-Asp(OtBu)-Ala-Ala-Val-Asp(OtBu)-Thr(TBu)-Ser(tBu)-Ser(tBu)-Glu(OtBu)-OC$_6$H$_5$
wherein Boc is tert.butyloxycarbonyl and tBu is tert.butyl.

5. A compound of the formula
Boc-Ser(tBu)-Asp(OtBu)-Ala-Val-Val-Asp(OtBu)-Thr(tBu)-Ser(tBu)-Ser(tBu)-Glu(OtBu)-OH
wherein Boc is tert.butyloxycarbonyl and tBu is tert.butyl.

* * * * *